(12) United States Patent
Jochelson et al.

(10) Patent No.: US 11,013,712 B2
(45) Date of Patent: *May 25, 2021

(54) METHODS OF TREATING INSOMNIA USING A COMBINATION THERAPY OF LOW-DOSE DOXEPIN AND ZOLPIDEM

(75) Inventors: Philip Jochelson, San Diego, CA (US); Robert Mansbach, San Diego, CA (US); Michael Skinner, San Diego, CA (US); Neil B. Kavey, Chappaqua, NY (US)

(73) Assignee: Currax Pharmaceuticals LLC, Morristown, NJ (US)

( * ) Notice: Subject to any disclaimer, the term of this patent is extended or adjusted under 35 U.S.C. 154(b) by 728 days.

This patent is subject to a terminal disclaimer.

(21) Appl. No.: 13/612,328

(22) Filed: Sep. 12, 2012

(65) Prior Publication Data

US 2013/0005655 A1 Jan. 3, 2013

Related U.S. Application Data

(63) Continuation of application No. 12/517,507, filed as application No. PCT/US2007/086682 on Dec. 6, 2007, now abandoned.

(60) Provisional application No. 60/873,056, filed on Dec. 6, 2006, provisional application No. 60/910,586, filed on Apr. 6, 2007.

(51) Int. Cl.

| *A61K 31/335* | (2006.01) |
| *A61K 31/343* | (2006.01) |
| *A61K 31/4162* | (2006.01) |
| *A61K 31/437* | (2006.01) |
| *A61K 31/4535* | (2006.01) |
| *A61K 31/4985* | (2006.01) |
| *A61K 31/505* | (2006.01) |
| *A61K 31/55* | (2006.01) |
| *A61K 45/06* | (2006.01) |
| *A61K 9/20* | (2006.01) |
| *A61K 9/28* | (2006.01) |
| *A61P 25/00* | (2006.01) |
| *A61P 25/20* | (2006.01) |

(52) U.S. Cl.
CPC .......... *A61K 31/335* (2013.01); *A61K 31/343* (2013.01); *A61K 31/4162* (2013.01); *A61K 31/437* (2013.01); *A61K 31/4535* (2013.01); *A61K 31/4985* (2013.01); *A61K 31/505* (2013.01); *A61P 25/00* (2018.01); *A61P 25/20* (2018.01)

(58) Field of Classification Search
CPC ............ A61K 2300/00; A61K 31/4985; A61K 31/343; A61K 31/4162; A61K 31/437; A61K 31/4535; A61K 45/06; A61K 31/4184; A61K 31/165; A61K 31/551; A61K 31/137; A61K 31/196; A61K 31/27; A61K 31/4525; A61K 31/5513; A61K 31/5517; A61K 31/00; A61K 31/138; A61K 31/192; A61K 31/216; A61K 31/404; A61K 31/405; A61K 31/4196; A61K 31/49; A61K 31/495; A01N 37/36

See application file for complete search history.

(56) References Cited

U.S. PATENT DOCUMENTS

| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Müller |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Adamczyk et al. |
| 5,502,047 A * | 3/1996 | Kavey ............... A61K 31/00 514/183 |
| 5,585,115 A | 12/1996 | Sherwood et al. |
| 5,643,897 A * | 7/1997 | Kavey ............... A61K 31/496 514/183 |
| 5,725,883 A | 3/1998 | Staniforth et al. |
| 5,725,884 A | 3/1998 | Sherwood et al. |
| 5,733,578 A | 3/1998 | Hunter et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,103,219 A | 8/2000 | Sherwood et al. |
| 6,106,865 A | 8/2000 | Staniforth et al. |
| 6,211,229 B1 * | 4/2001 | Kavey ............... A61K 31/13 514/217 |

(Continued)

FOREIGN PATENT DOCUMENTS

| WO | WO 1999/40898 | 8/1999 |
| WO | WO 2000/010554 | 3/2000 |

(Continued)

OTHER PUBLICATIONS

Pinder et al. Drug, 1977; 13:161-218.*
Roehrs et al. Sleep Medicine 2004; 5: 463-466.*
Kelsay J. Allergy Clin. Immunol. 2006, 118: 198-201.*
Silber New Engl.J. Med. Silber 2005; 353:803-10.*
Millan et al. J. Pharmacol. Exp. Ther. 2003; 306: 954-964.*
The factsheet of Zolpidem tartrate (Intermezzo®) approved by the FDA (retrieved from the FDA website: www.accessdata.fda.gov/drugsatfda_docs/label/2011/022328lbl.pdf on Feb. 18, 2020.*
Lie et al. P&T, 2015 40:759-771.*

(Continued)

*Primary Examiner* — Chang-Yu Wang
(74) *Attorney, Agent, or Firm* — Servilla Whitney LLC

(57) ABSTRACT

A composition comprising doxepin, or a pharmaceutically acceptable salt, or prodrug thereof, and a compound that enhances sleep onset, sleep maintenance or reduces early morning awakenings. These compositions are useful for treating multiple manifestations of insomnia.

9 Claims, No Drawings

(56) References Cited

U.S. PATENT DOCUMENTS

| | | | |
|---|---|---|---|
| 6,217,907 B1 | 4/2001 | Hunter et al. | |
| 6,217,909 B1 | 4/2001 | Sherwood et al. | |
| 6,219,674 B1 | 4/2001 | Classen | |
| 6,344,487 B1 | 2/2002 | Kavey | |
| 6,358,533 B2 | 3/2002 | Sherwood et al. | |
| 6,391,337 B2 | 5/2002 | Hunter et al. | |
| 6,395,303 B1 | 5/2002 | Staniforth et al. | |
| 6,403,597 B1 | 6/2002 | Wilson et al. | |
| 6,407,128 B1 | 6/2002 | Scaife et al. | |
| 6,471,994 B1 | 10/2002 | Staniforth et al. | |
| 6,514,531 B1* | 2/2003 | Alaux | A61K 31/496 424/468 |
| 6,521,261 B2 | 2/2003 | Sherwood et al. | |
| 6,583,285 B1* | 6/2003 | Sauter | C07C 235/74 546/121 |
| 6,584,472 B2 | 6/2003 | Classen | |
| 6,638,535 B2* | 10/2003 | Lemmens | A61K 9/1652 424/464 |
| 6,683,102 B2 | 1/2004 | Scaife et al. | |
| 6,746,693 B2 | 6/2004 | Staniforth et al. | |
| 6,761,910 B1* | 7/2004 | Pettersson | A61K 31/34 424/489 |
| 6,852,336 B2 | 2/2005 | Hunter et al. | |
| 6,858,231 B2 | 2/2005 | Sherwood et al. | |
| 6,866,867 B2 | 3/2005 | Staniforth et al. | |
| 6,921,839 B2* | 7/2005 | Kumar | C07C 231/02 564/139 |
| 6,936,277 B2 | 8/2005 | Staniforth et al. | |
| 7,135,196 B2 | 11/2006 | Stockham | |
| 7,179,488 B2 | 2/2007 | Sherwood et al. | |
| 7,276,536 B2 | 10/2007 | Urata et al. | |
| 7,425,556 B2* | 9/2008 | Chapdelaine et al. | 514/248 |
| 7,452,872 B2 | 11/2008 | Johnson | |
| 7,465,795 B2* | 12/2008 | Chapdelaine et al. | 544/235 |
| 7,863,296 B2* | 1/2011 | Weiner et al. | 514/317 |
| 7,915,307 B2* | 3/2011 | Casseday | A61K 31/55 514/450 |
| 8,097,625 B2* | 1/2012 | Lalji | A61K 31/137 514/247 |
| 8,242,131 B2* | 8/2012 | Singh | A61K 9/2018 514/294 |
| 8,252,809 B2* | 8/2012 | Singh | A61K 9/0058 514/294 |
| 8,513,299 B2* | 8/2013 | Rogowski | A61K 31/335 514/450 |
| 8,598,119 B2* | 12/2013 | Mates et al. | 514/11.4 |
| 9,107,898 B2* | 8/2015 | Rogowski | A61K 31/335 |
| 9,486,437 B2* | 11/2016 | Rogowski | A61K 31/335 |
| 9,801,847 B2* | 10/2017 | Dube | A61K 31/335 |
| 9,861,607 B2* | 1/2018 | Rogowski | A61K 31/335 |
| 10,143,676 B2* | 12/2018 | Dube | A61K 31/335 |
| 10,238,620 B2* | 3/2019 | Rogowski | A61K 31/335 |
| 10,251,859 B2* | 4/2019 | Dube | A61K 31/335 |
| 2002/0037828 A1 | 3/2002 | Wilson et al. | |
| 2002/0183522 A1* | 12/2002 | Sauter | C07D 471/04 546/112 |
| 2002/0197235 A1 | 12/2002 | Moran | |
| 2003/0181353 A1* | 9/2003 | Nyce | 514/1 |
| 2003/0206978 A1 | 11/2003 | Sherwood et al. | |
| 2003/0235617 A1 | 12/2003 | Martino et al. | |
| 2004/0063721 A1 | 4/2004 | Deecher et al. | |
| 2004/0087794 A1* | 5/2004 | Sauter | C07C 235/78 546/121 |
| 2004/0115142 A1 | 6/2004 | Sherwood et al. | |
| 2004/0224017 A1 | 11/2004 | Mulye | |
| 2004/0265374 A1 | 12/2004 | Staniforth et al. | |
| 2005/0013861 A1 | 1/2005 | Sherwood et al. | |
| 2005/0054669 A1* | 3/2005 | Kumar | C07D 471/04 514/303 |
| 2005/0118261 A1 | 6/2005 | Oien et al. | |
| 2005/0123609 A1 | 6/2005 | Hirsh et al. | |
| 2005/0143348 A1* | 6/2005 | Edgar | A61K 31/452 514/89 |
| 2005/0147673 A1 | 7/2005 | Staniforth et al. | |
| 2005/0171160 A1 | 8/2005 | Edgar et al. | |
| 2005/0196439 A1 | 9/2005 | Sherwood et al. | |
| 2005/0214365 A1 | 9/2005 | Yousef et al. | |
| 2005/0239838 A1 | 10/2005 | Edgar et al. | |
| 2005/0256165 A1 | 11/2005 | Edgar et al. | |
| 2006/0008522 A1 | 1/2006 | Staniforth et al. | |
| 2006/0009465 A1* | 1/2006 | Edgar | A61K 31/00 514/253.04 |
| 2006/0228487 A1 | 10/2006 | Schaible | |
| 2006/0239928 A1* | 10/2006 | Heit | A61K 9/006 424/45 |
| 2007/0142328 A1* | 6/2007 | Chapdelaine et al. | 514/63 |
| 2007/0142382 A1* | 6/2007 | Chapdelaine et al. | 514/248 |
| 2007/0281990 A1* | 12/2007 | Rogowski et al. | 514/450 |
| 2008/0058407 A1 | 3/2008 | Baron et al. | |
| 2008/0058408 A1* | 3/2008 | Rogowski | A61K 31/335 514/450 |
| 2008/0132535 A1* | 6/2008 | Singh | A61P 25/20 514/300 |
| 2008/0145425 A1* | 6/2008 | Marija | A61P 25/00 424/482 |
| 2008/0182890 A1 | 7/2008 | Jochelson et al. | |
| 2009/0042971 A1 | 2/2009 | Rogowski et al. | |
| 2009/0042972 A1 | 2/2009 | Rogowski et al. | |
| 2009/0074862 A1 | 3/2009 | Schioppi et al. | |
| 2010/0105614 A1* | 4/2010 | Jochelson | A61K 31/4985 514/1.1 |
| 2010/0179214 A1 | 7/2010 | Dubè et al. | |
| 2010/0179215 A1* | 7/2010 | Dube | A61K 31/335 514/450 |
| 2010/0227916 A1* | 9/2010 | Kavey | A61P 25/20 514/450 |
| 2011/0077200 A1 | 3/2011 | Jochelson et al. | |
| 2011/0166215 A1 | 7/2011 | Casseday et al. | |
| 2011/0178166 A1 | 7/2011 | Rogowski et al. | |
| 2011/0318412 A1 | 12/2011 | Schioppi et al. | |
| 2012/0088822 A1 | 4/2012 | Rogowski et al. | |
| 2012/0245222 A1 | 9/2012 | Rogowski et al. | |
| 2013/0041021 A1* | 2/2013 | Casseday | A61K 31/55 514/450 |
| 2013/0150434 A1* | 6/2013 | Jochelson | A61K 31/335 514/450 |
| 2013/0259936 A1* | 10/2013 | Schioppi | A61K 9/2009 424/465 |
| 2014/0107084 A1* | 4/2014 | Jochelson | A61K 31/343 514/171 |
| 2017/0157140 A1* | 6/2017 | Casseday | A61K 31/55 |
| 2018/0256533 A1* | 9/2018 | Schioppi | A61K 9/2009 |
| 2019/0099396 A1* | 4/2019 | Dube | A61K 31/335 |
| 2019/0216766 A1* | 7/2019 | Rogowski | A61K 31/335 |
| 2019/0231734 A1* | 8/2019 | Dube | A61K 31/335 |

FOREIGN PATENT DOCUMENTS

| | | |
|---|---|---|
| WO | WO 2000/050025 | 8/2000 |
| WO | WO 2003/004009 | 1/2003 |
| WO | WO 2003/047519 | 6/2003 |
| WO | WO 2003/066029 | 8/2003 |
| WO | WO 2007/136845 | 11/2007 |
| WO | WO 2007/142810 | 12/2007 |
| WO | WO2007/142811 | * 12/2007 |
| WO | WO 2007/142811 | 12/2007 |

OTHER PUBLICATIONS

The factsheet of a Study of Zolpidem Tartrate Sublingual Tablet in Adult Patients With Insomnia from the NIH Clinical Trial website: clinicaltrials.gov/ct2/show/NCT00380081, retrieved on Jun. 16, 2020.*
Seainston et al. CNS Drugs, 2005; 19:65-89.*
Kelsay, J. Allergy Clin. Innnnunol. 2006; 118:198-201.*
Krystal et al. Sleep; 2010; 33:1553-1561.*
Hajak et al., J. Clin. Psychiatry. 2001;62:453-463; abstract.*
Kvale et al. J. Palliative Med. 2006; 9:437-450.*
Verster et al. Sleep Med. Rev. 2004; 8:309-325.*
The factsheet of Low-Dose doxepin phase II clinical trial from Somaxon pharmaceuticals website. pbulished Apr. 21, 2005.*

(56) References Cited

OTHER PUBLICATIONS

Roth et al. Sleep, 2007; 30:1555-1561.*
Abernethyl et al., Absolute bioavailability of imipramine: Influence of food, Psychopharmacology (Berl), 1984; 83(1):104-106.
ABPI (Association of the British Pharmaceutical Industry) Compendium of Data Sheets & SmPC's, 1999-2000; Pfizer Limited, p. 1158.
ABPI (Association of the British Pharmaceutical Industry) Compendium of Data Sheets and Summaries of Product Characteristics, 1996-1997; Pfizer Limited, p. 751-752.
ABPI (Association of the British Pharmaceutical Industry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1998-1999; Pfizer Limited, p. 970-971.
ABPI (Association of the British Pharmaceutical Industry) Medicines Compendium, 2002; Pfizer Limited, p. 1792-1793.
Adamzyk et al., Quantitative determination of E- and Z-doxepin and E- and Z-desmethyldoxepin by high-performance liquid chromatography. Ther Drug Monit. 17(4):371-6 (1995).
ADAPIN, Drug Side Effects, www.depression-guide.com/adapin.htm, 2005, 1-3.
Albemarle Pulmonary Medicine Associates, apma-nc.com/PatientEducation/INSOMNIA.HTM, 2000, pp. 1-4.
AMBIEN (Zolpidem Tartrate) tablets CIV. Highlights of Prescribing Information. Revised Jun. 2009. Sanofi-Aventis U.S. LLC. p. 1-18.
AMBIEN (Zolpidem Tartrate) tablets CIV. Prescribing Information. Revised Jun. 2008. Sanofi-Aventis U.S. LLC. p. 1-22.
AMBIEN CR (zolipidem tartrate extended-release). Highlights of Prescribing Information. Package Insert. Jan. 2008, Sanofi-Aventis U.S. LLC. p. 1-7.
AMBIEN CR (zolpidem tartrate extended release) tablets—CIV. Full Prescribing Information. Sep. 2009. Web download: Jul. 6, 2010. products.sanofi-aventis.us/ambien_cr/ambiencr.html. p. 1-32.
AMBIEN CR (zolpidem tartrate extended release). Healthcare Professional Information. Healthcare Professionals. Help your insomnia patients meet the day on. Web download: Jul. 6, 2010. www.ambiencr.com/hcp/zolpidem-tartrate.aspx. p. 1-2.
Ancoli-Israel et al., Identification and Treatment of Sleep Problems in the Elderly, Review Article, Sleep Medicine Reviews, 1(1): 3-17, (1997).
ANON, Quitaxon 10 mg cp pellic séc. [Online] (2006), XP002507206, Retrieved from the Internet: URLwww.vidal.fr/Medicament/quitaxon-14133.htm> [retrieved on Dec. 8, 2008].
Approval data of the German drug regulatory authorities. DIMDI: AMIS—Public Part (AJ29). German Institute of Medical Documentation and Information within the scope of the Federal Ministry of Health. Pfizer Pharma GmBH. Sinquan 10 mg; capsules, SINQUAN 100; capsules; Sinquan 100 mg; capsules, SINQUAN 25 INTRA-MUSCULAR; solution; Sinquan 25 mg; capsules, Sinquan 50 mg; capsules, Sinquan 75 mg; capsules. Retrieved Nov. 16, 2005 from gripsdb.dimdi.de/session/0511161521292992047/13docs.htm.
Badenhorst et al., Determination of doxepin and desmethyldoxepin in human plasma using liquid chromatography-tandem mass spectrometry. J Chromatogr B Biomed Sci Appl. 742(1):91-8 (2000).
Baldrick, Pharmaceutical excipient development: the need for preclinical guidance. Regul Toxicol Pharmacol. 32(2): 210-218 (2000).
Becker, Pharmacologic and Nonpharmacologic Treatments of Insomnia, Neurol Clin. 23: 1149-1163 (2005).
Biggs et al., Dosage schedule and plasma levels of doxepin and desmethyldoxepin. J Clin Psychiatry. 39(10):740-2 (1978).
Bogaert et al. Plasma levels of the cis- and trans-isomers of doxepin and desmethyldoxepin after administration of doxepin to patients. Arzneimittelforschung. 31(1):113-5 (1981).

Brunello et al., Effect of Some Tricyclic and Nontricyclic Antidepressants on [H]Imiipramine Binding and Serotonin Uptake in Rat Cerebral Cortex After Prolonged Treatment. Fundam Clin Pharmacol. 1: 327-333 (1987).
Brunswick et al. Relationship between tricyclic antidepressant plasma levels and clinical response in patients treated with desipramine or doxepin. Acta Psychiatr Scand. 67(6):371-7 (1983).
Bundgaard, Ed. Design of Prodrugs: Bioreversible derivatives for various functional groups and chemical entities, Elsevier, Amsterdam (1985). Chapter 1. p. 1-92.
Burch et al., Amitriptyline pharmacokinetics. A crossover study with single doses of amitriptyline and nortriptyline, Psychopharmacology (Berl), 1981; 74(1):35-42.
CBS.com, Ambien May Prompt Sleep-Eating; www.cbsnews.com/stories/2006/03/15/early show/health/ (2 pages).
Charman, Lipids, Lipophilic Drugs, and Oral Drug Delivery—Some Emerging Concepts. J Pharm Sci .89(8):967-78 (2000).
Chen, Sleep, Depression and Antidepressants, British Journal of Psychiatry, 135: 385-402, (1979).
Chloral Hydrate Drug Information, Professional. Chloral Hydrate (Systemic). Drug Information Online. Drugs.com. Web download: Jul. 6, 2010. www.drugs.com/mmx/chloral-hydrate.html. p. 1-15.
Claudino et al., Antidepressants for Anorexia Nervosa (Review). Cochrane Database Syst Rev., John Wiley & Sons, Ltd., 1:1-39 (2006).
Conn et al., Pattern of Use of Antidepressants in Long-Tern Care Facilities for the Elderly, Journal of Geriatric Psychiatry and Neurology, vol. 5:4, p. 228-232, (1992).
Declerck et al., Increase in Slow-wave Sleep in Humans with the Serotonin-S2 Antagonist Ritanserin. Curr Ther Res., 41(4): 427-432 (1987).
DESYREL—trazadone hydrochloride tablet. Bristol-Myers Squibb Company. Prescribing Information. Revised Feb. 2009. p. 1-9.
Deuschle et al., Doxepin and its Metabolites in Plasma and Cerebrospinal Fluid in Depressed Patients, Psychopharmacology, 131(1): 19-22, (1997).
Dilger et al. High-performance liquid chromatographic determination of trans-doxepin and desmethyldoxepin. Arzneimittelforschung. 38(10):1525-8 (1988).
DOXAL. Lääkeopas. Retrieved Nov. 28, 2005 from www.coronaria.fi/www/mtv3/laakkeet.php?id=299.
DOXAL. Lääkkeet. Retrieved Nov. 28, 2005 from www.tohtori.fi/laakkeet/tuote.php3?ID=412.
DOXEPIN. Find Treatment & Support. The most reliable cancer treatment information. Cancer.org. Web download: Jul. 6, 2010. www.cancer.org/docroot/CDG/content/CDG_doxepin.asp?internal=1. p. 1-6.
Dugovic et al., 5-HT2 Receptors could be Primarily Involved in the Regulation of Slow-wave Sleep in the Rat. Euro J Pharma., 137: 145-146 (1987).
Dunleavy et al., Changes During Weeks in Effects of Tricyclic Drugs on the Human Sleeping Brain, British Journal of Psychiatry, 120: 663-672, (1972).
Ebert et al., Treating insomnia: Current and investigational pharmacological approaches. Pharmacol Thera., 112(3): 612-629 (Mar. 2006).
ELAVIL—Amitriptyline Hydrochloride—amitriptyline hydrochloride tablet, film coated. Mutual Pharmceutical Company, Inc. Revised Sep. 2007. p. 1-9.
Ereshefsky et al., Pharmacokinetic factors affecting antidepressant drug clearance and clinical effect: evaluation of doxepin and imipramine—new data and review. Clin Chem. 34(5):863-80 (1988).
Erman et al., Comparative Efficacy of Zolpidem and Temazepam in Transient Insomnia, Human Psychopharma Clin Exp., 16: 169-176 (2001).
Faulkner et al., Comparative assays for doxepin and desmethyldoxepin using high-performance liquid chromatography and high-performance thin-layer chromatography. J Pharm Sci. 72(10):1165-7 (1983).
Faulkner et al., Multiple-dose doxepin kinetics in depressed patients. Clin Pharmacol Ther. 34(4):509-15 (1983).
Fava, Weight Gain and Antidepressants. J Clin Psychiatry., (61 Suppl) 11: 37-41, (2000).

(56) References Cited

OTHER PUBLICATIONS

Fawcett et al., Review of the Results from Clinical Studies on the Efficacy, Safety and Tolerability of Mirtazapine for the Treatment of Patients with Major Depression J. Affective Disorders (1998) 51: 267-285.
Friedel et al. Relationship of blood levels of sinequan to clinical effects in the treatment of depression in aged patients. In. Mendels J, editor. Amsterdam: Excerpta Medica. p. 51-53 (1975).
Fulton et al., Assessment of the Antidepressant Activity of Dothiepin and its Metabolites by Preclinical Tests. J Affect Dis. 4: 261-269 (1982).
Georgotas et al., Response of Depressive Symptoms to Nortriptyline, Phenelzine and Placebo, Br. J. Psychiatry (1987) 151: 102-106.
German Federal Gazette (BAnz) No. 240 of Dec. 22, 1992, p. 9545 (vol. 44).
Ghabrial et al., Geometric isomerization of doxepin during its N-demethylation in humans. Drug Metab Dispos. 19(3):596-9 (1991).
Gillin et al., Successful Separation of Depressed, Normal, and Insomniac Subjects by EEG Sleep Data, Arch Gen Psychiatry, vol. 36, p. 85-90, (1979).
Green, Douglas O., Clinical importance of doxepin antidepressant plasma levels. J Clin Psychiatry. 39(5):481-2 (1978).
Grundstrom et al., Sedative Properties of Doxepin in Comparison with Diazepam, Psychopharmacology, 54: 165-169 (1977).
Guidance for Industry SUPAC-IR/MR: Immediate Release and Modified Release Solid Oral Dosage Forms—Manufacturing Equipment Addendum, Jan. 1999.
Hajak et al., Nocturnal Melatonin Secretion and Sleep after Doxepin Administration in Chronic Primary Insomnia, Pharmacopsychiatry 29: 187-192, (1996).
HALCION—Triazolam tablet. Pharmacia and Upjohn Company. Prescribing Information. Revised Jan. 2009. p. 1-10.
Haritos et al., Role of cytochrome P450 2D6 (CYP2D6) in the stereospecific metabolism of E- and Z-doxepin. Pharmacogenentics. 10(7):591-603 (2000).
Haritos et al., Stereoselective measurement of E- and Z-doxepin and its N-desmethyl and hydroxylated metabolites by gas chromatography-mass spectrometry. J Chromatogr B Biomed Sci Appl. 736(1-2):201-8 (1999).
Hartmann et al., The Effects of Long Term Administration of Psychotropic Drugs on Human Sleep: III. The Effects of Amitriptyline, Psychopharmacologia, 33: 185-202 (1973).
Hartmann, Peter M., Clinical Pharmacology—Miratzapine: A Newer Antidepressant, American Family Physician (1999) 1-5.
Hartter et al., The N-demethylation of the doxepin isomers is mainly catalyzed by the polymorphic CYP2C19. Pharm Res. 19(7):1034-7 (2002).
Haute Autorite De Sante (France): Avis Dec. 13, 2006 [Online] 2006, XP002507207; Retrieved from the Internet: URL:www.has-sante.fr/portail/jcms/c_475580/quitaxon> [retrieved on Dec. 8, 2008].
Heal et al., Comparative Pharmacology of Dothiepin, its Metabolites, and other Antidepressant Drugs. Drug Dev Res. 27: 121-135 (1992).
Hellberg et al., The Hydrolysis of the Prostaglandin Analog Prodrug Bimatoprost to 17-Phenyl-Trinor PGF2 by Human and Rabbit Ocular Tissue. J Ocul Pharmacol Ther., 19(2): 97-103 (2003).
Higuchi et al., Pro-Drugs as Novel Delivery Systems, A.C.S. Symposium Series, American Chemical Society; vol. 14, (1975)—Title Pages Only.
Hobbs, Distribution and Metabolism of Doxepin, Biochem. Pharmacol., 18(8): 1941-1954, (1969).
Hohagen et al., Treatment of Primary Insomnia with Trimipramine: An Alternative to Benzodiazepine Hypnotics? Eur Arch Psychiatry Clin Neurosci. 244(2): 65-72 (1994).
Hrdina et al., Antidepressant plasma levels and clinical response in depressed patients treated with oxaprotiline and doxepin. Int Clin Psychopharmacol. July;3(3):205-14 (1988).
Hrdina et al., Cis- and trans-isomers of doxepin and desmethyldoxepin in the plasma of depressed patients treated with doxepin. Ther Drug Monit. 12(2):129-33 (1990).
Hsu et al., Low-Dose Doxepin in the treatment of primary insomnia, Sleep, 28: suppl, p. A50, (2005).
Jacobsen, Low-Dose Trazodone as a Hypnotic in Patients Treated with MAOls and Other Psychotropics: A Pilot Study, Journal of Clinical Psychiatry, 51: 298-392 (1990).
Joyce et al., Doxepin plasma concentrations in clinical practice. Could there be a pharmacokinetic explanation for low concentrations? Clin Pharmacokinet. 10(4):365-70 (1985).
Kales et al., Effects of Sinequan on sleep of Insomniac Subjects, Sleep Study Abstracts, p. 93, (1972).
Kirchheiner et al., Contributions of CYP2D6, CYP2C9 and CYP2C19 to the biotransformation of E- and Z-doxepin in healthy volunteers. Pharmacogenetics. 12(7):571-80 (2002).
Kline et al., Doxepin and Desmethyldoxepin Serum Levels and Clinical Response. In: Gottschalk LA MM, editor. Pharmacokinetics of psychoactive drugs: blood levels and clinical response. New York: Spectrum Press. p. 221-228 (1976).
Krakowski. Seminar on Psychopharmacology—Auspices of Academy of Psychosomatic Medicine, Dec. 8-9, 1968 Freeport, Grand Bahama Island, Psychosomatics, pp. 7-63 (1968).
Laimer et al., Effect of Mirtazapine Treatment on Body Composition and Metabolism, J Clin Psychiatry, 67(3): 421-524 (2006).
Lapp, Chronic Fatigue Syndrome is a Real Disease, North Carolina Family Physician, 43:1, (1992).
Leucht et al., Doxepin plasma concentrations: is there really a therapeutic range? J Clin Psychopharmacol. 21(4):432-9 (2001).
Linnoila et al., Clomipramine and doxepin in depressive neurosis. Plasma levels and therapeutic response. Arch Gen Psychiatry. 37(11):1295-9 (1980).
Luchtefeld, Answers to the Most Common Questions Regarding Prescription Drugs—Safeguard Your Health, Jenry Consulting 1999, www.grandtimes.com/Answer_Drugs.html, 1-3.
LUNESTA (Eszopiclone) Tablets 1 mg, 2 mg, 3 mg. Prescribing Information. Package Insert. Sepracor Inc. Jan. 2009. p. 1-2.
Luo et al., The Quaternary Ammonium-Linked Glucuronide of Doxepin: A Major Metabolite in Depressed Patients treated with Doxepin. Drug Metab Dispos., 19(3): 722-724, (1991).
Manning et al., Central Nervous System Effects of Meclizine and Dimenhydrinate: Evidence of Acute Tolerance to Antihistamines. J. Clin. Psychiatry 32:996-1002 (1992).
Masaki et al., Involvement of Hypothalamic Histamine H1 Receptor in the Regulation of Feeding Rhythm and Obesity, Diabetes 53(9): 2250-2260, (2004).
Masaki et al., The Hypothalamic H1 Receptor: A Novel Therapeutic Target for Disrupting Diurnal Feeding Rhythm and Obesity. Trends Pharmacol Sci. 27(5): 279-284, (2006).
Mayers et al., Antidepressants and their effect on sleep, Hum Psychopharmacol., 20(8): 533-559 (Dec. 2005).
Mealy et al., Drugs Under Development for the Treatment of Psychiatric Disorders. Drugs Fut. 31(3): 266-284 (2006).
Mercer et al., Dietary Induced Anorexia: A Review of Involvement of the Histominergic System, J Am Coll Nutr., 15(3): 223-230, (1996).
Midha et al., Stereoselective pharmacokinetics of doxepin isomers. Eur J Clin Pharmacol. 42(5):539-44 (1992).
Moody et al., Biotransformation of Doxepin by *Cunninghamella elegans*, Drug Metab Dispo., 27(10): 1157-1164, (1999).
Narasimhachari et al., N-Alkylation of Secondary Amine Tricyclic Antidepressants as a General Method for Their Quantitation by GC-MS-SIM Technique. Analytical Lett. 12(61): 77-88 (1979).
National Academy of Sciences, Sleeping Pills, Insomnia, and Medical Practice, Institute of Medicine, 32-33,103,125,149,169,198, (1979).
Natrol Melatonin 3 mg. 60 Tablets. Dietary Supplement. Manufactured by Natrol, Inc. Label. p. 1-3.
Neubauer, Sleep Problems in the Elderly. Am Fam Physician. 59(9): 2551-2558 (May 1999).
New Drug Application 16-798 for SINEQUAN approved in 1978 (includes evaluation of insomnia indication on pp. 46-47, 54, 57, 59.
Newcomer et al., The Metabolic Effects of Antipsychotic Medications, Can J Psychiatry. 51(8): 480-491 (2006).
Nicholson et al., Modulation of sleep by trimipramine in man, European Journal of Clinical Pharmacol, 37: 145-150, (1989).

(56) References Cited

OTHER PUBLICATIONS

Nierenberg et al., Management of Monoamine Oxidase Inhibitor-Associated Insomnia with Trazodone, Journal of Clinical Psychopharmacol, vol. 9 No. 1, p. 42-45, (1989).
NyQuil Cold & Flu. Nightime Relief. Acetaminophen, Doxylamine, Dextromethorphan, Alcohyl 10%. 6 Fl Oz. Vicks Label. 2 pages.
NyQuil Oral. Drugs & Medications. WebMD. Web download: Jul. 6, 2010. www.webmd.com/drugs/drug-6104-NyQuil+Oral.aspx?drugid=6104&drugname=NyQuil+Oral&source=1. p. 1-3.
NYTOL Oral. Drugs & Medications—WebMD. Web download: Jul. 6, 2010. www.webmd.com/drugs/drug-10538-Nytol+Oral.aspx?drugid=10538&drugname=Nytol+Oral&source=0. p. 1-2.
NYTOL Quickcaps with Diphenhydramine HCI. Nightime Sleep-Aid. 72 Caplets. Label. 4 pages.
O'Brien et al., GLC determination of doxepin plasma levels. J Pharm Sci. 65(7):1068-9 (1976).
Ookuma et al., Evidence for Feeding Elicited Through Antihistaminergic Effects of Tricyclic Antidepressants in the Rat Hypothalamus. Psychopharmacology (Berl). 101(4): 481-485, (1990).
Orthen-Gambill et al., Differential Effects of Psychotropic Drugs on Feeding in Rats: Is Histamine Blockade Involved? Pharmacol Biochem Behav., 36(4): 837-841 (1990).
Orthen-Gambill, Antihistaminic Drugs Increase Feeding, While Histidine Suppresses Feeding in Rats, Pharmacol Biochem Behav., 31(1): 81-86, (1988).
Pälvimäki et al. Interactions of selective serotonin reuptake inhibitors with the serotonin 5-HT2C receptor. Phychopharmacology, 126(3): 234-240 (1996).
Patent Information Leaflet, Sinequan™ (doxepin), United Kingdom, p. 1-2 (2002).
Pecknold et al., Trimipramine, Anxiety, Depression and Sleep, Drugs, vol. 38: Suppl. 1, p. 25-31, (1989).
Pfizer, Chemist Review of NDA 17-516, Division of Neurophamacological Drug Products, Chemists Review #3, (1973).
Pharmaca Fennica. Published by the Finnish Centre for Medicine Information (Lääketietokeskus); SR Doxal; (1992).
Pharmaca Fennica. Published by the Finnish Centre for Medicine Information (Lääketietokeskus); SR Doxal; 612-613 (1988).
Pharmaca Fennica. Published by the Finnish Centre for Medicine Information (Lääketietokeskus); SR Doxal; 714 (1991).
Pharmaca Fennica. Published by the Finnish Centre for Medicine Information (Lääketietokeskus); SR Doxal; 738 (1993).
Pharmaca Fennica. Published by the Finnish Centre for Medicine Information (Lääketietokeskus); SR Doxal; 830 (1995).
Pharmaca Fennica. Published by the Finnish Centre for Medicine Information (Lääketietokeskus); Ye R Doxal; 534-535 (2000).
Pharmaca Fennica. Published by the Finnish Centre for Medicine Information (Lääkevalmisteet); SR SINEQUAN; 845-846 (1993).
Pharmassure. Standardized. Valerian. Herbal Supplement. Minimumum 0.8% Valerenic Acids (2mg). 250 mg. 60 Softgel Capsules. Distributed by PharmAssure, Inc. Label. p. 1-4.
Phillips et al., Sleep Disorders in the Elderly, Sleep Medicine 2: 99-114 (2001).
Physician's Desk Reference, 1999 ed., Medical Economics Company, Montvale NJ pp. 539-541 (Trazadone).
Physician's Desk Reference, 2000 ed., Medical Economics Company, Montvale NJ pp. 2366-2367 (Doxepine HCI).
Physician's Desk Reference, 2000 ed., Medical Economics Company, Montvale NJ pp. 3323-3324 (Trimipramine maleate).
Physician's Desk Reference, 2000 ed., Medical Economics Company, Montvale NJ pp. 549-551 (Amitriptyline HCI).
Physicians Desk Reference, Litton Industries, p. 1211, 93, (1976).
Physicians' Desk Reference, p. 1310-1312, (1990).
Physicians' Desk Reference, p. 1849-1850, (1990).
Physicians' Desk Reference, p. 2434-2435, (1990).
Pinder et al., Doxepin up-to-date: a review of its pharmacological properties and therapeutic efficacy with particular reference to depression. Drugs. 13(3):161-218 (1977).
Polish Drug Application for SINEQUAN 10 mg capsules. 01474/93. p. 1-4 with attached Annex in 4 pages.
Polish Drug Application for SINEQUAN 25 mg capsules. 01475/93. p. 1-4 with attached Annex in 4 pages.
Pollack, Is Biotechnology Losing Its Nerve?, NY Times (Feb. 29, 2004), pp. 1-4.
Powell et al. Compendium of Excipients for Parenteral Formulations, PDA J Pharm Sci Technol. 52(2): 238-311 (1998).
Prakash et al. Deuterium Labelling of the Antidepressant Drug Doxepin for Disposition Studies in Human Subjects. J Lab Comp Radiopharma. 28(9): 1037-47 (1990).
Remington: The Science and Practice of Pharmacy, 21st Ed., Lippincott Williams & Wilkins (2006). Table of Contents Only.
RESTORIL—Temazepam capsule. Mallinckrodt Inc. Prescribing Information. Revised Mar. 2006. p. 1-8.
Ribbentrop et al., Pharmacologic studies of doxepin, an antidepressive agent with centrally anticholinergic and sedative effects. Arzneimittelforschung. 15:863-68 (1965). Translation of Abstract only.
Richardson et al., Tolerance to Daytime Sedative Effects of H1 Antihistamines. J Clin Psychopharmacol. 22(5): 511-515 (2002).
Richelson et al., Antagonism by Antidepressants of Neurotransmitter Receptors of Normal Human Brain in Vitro, J Pharmacol Exp Ther. 230(1): 94-102 (1984).
Richelson, Tricyclic Antidepressants and Histamine H1 Receptors, Mayo Clin Proc., 54:669-674, (1979).
Roche, Bioreversible Carriers in Drug Design: Theory and Application, Pergamon Press: New York, pp. 14-21 (1987)—Contents Pages Only.
Rosseel et al., Quantitative GLC determination of cis- and trans-isomers of doxepin and desmethyldoxepin. J Pharm Sci. 67(6):802-5 (1978).
Roth et al., Efficacy and Safety of doxepin 1, 3 , and 6mg in elderly adults with primary insomnia, Sleep (Rochester),29: suppl. S (2006).
Roth et al., Efficacy and Safety of Doxepin 1mg, 3mg , and 6mg in Adults with Primary Insomnia, Sleep, 30(11): 1555-1561 (Nov. 2007).
Roth et al., Efficacy and Safety of Zolpidem-MR: A Double-Blind, Placebo-Controlled Study in Adults with Primary Insomnia, Sleep Med. 7(5): 397-406 (2006).
Roth et al., Psychopharmacolodgy: The Effects of Doxepin HCI on Sleep and Depression, Journal of Clinical Psychiatry, 43:9, p. 366-368 (1982).
ROZEREM (ramelteon) tablets. Highlights of Prescribing Information. Takeda Pharmaceuticals. Revised Oct. 2008. p. 1-6.
Saul, Stephanie, Study Links Ambien Use to Unconscious Food Forays, The New York Times www.nytimes.com/2006/03/14/health/14sleep.html (4 pages).
Scharf et al., Efficacy and Safety of Doxepin 1 mg, 3 mg, and 6 mg in Elderly Patients With Primary Insomnia: A Randomized, Double-Blind, Placebo-Controlled Crossover Study. J Clin Psychiatry 69(10): 1557-1564 (Oct. 2008).
Schatzberg et al., "Hypnotics" Manual of Clinical Psychopharmacology, American Psychiatric Press, Inc., Washington D.C., p. 173-189, (1986).
Schweitzer et al., Sleepiness and Performance During Three-Day Administration of Cetirizine or Diphenhydramine. J Allergy Clin Immunol. 94(4): 716-724 (1994).
Seifritz E. Contribution of Sleep Physiology to Depressive Pathophysiology, Neuropsychopharmacology 25(5) 51: S85-S88 (Nov. 2001).
Seminar on Psychosomatics, Auspices of Academy of Psychosomatic Medicine, p. 4-63 (1968).
Shu et al., The Identification of Urinary Metabolites of Doxepin in Patients. Drug Metabolism & Disposition, Drug Metabolism & Disposition, 18(5): 735-741 (1990).
Shu et al., Identification of Phenolic Doxepin Glucuronides from Patient Urine and Rat Bile. Drug Metab Disp. 18(6): 1096-1099 (1990).
SILENOR (doxepin) Drug Description. RXList: Apr. 2, 2010. p. 1.
SILENOR (doxepin) Prescribing Information. Revised Mar. 2010. p. 1-12.
SINEQUAN (doxepin HCI) Capsules Oral Concentrate. Prescribing Information. Revised Oct. 2008. p. 1-13.
SINEQUAN (Doxepin, Adapin): A guide to sinequan side effects. depression-guide.com. (2005). Web download: Jul. 6, 2010. www.depression-guide.com/sinequan.htm. p. 1-3.

(56) References Cited

OTHER PUBLICATIONS

SINEQUAN Dosage. eMEDTV. Clinaero, Inc. Updated/reviewed Apr. 2, 2007. Web download: Jul. 6, 2010. depression.emedtv.com/sinequan/sinequan-dosage.html. p. 1-2.
Sokoliess et al., Separation of (Z)- and (E)-isomers of thioxanthene and dibenz[b,e]oxepin derivatives with calixarenes and resorcinarenes as additives in nonaqueous capillary electrophoresis. Electrophoresis. 24(10):1648-57 (2003).
SOMAXON Pharmaceuticals Announces Acceptance for Filing of New Drug Application for SILENOR™ for the Treatment of Insomnia, Somaxon Pharmaceuticals Press Release, San Diego, CA, p. 1-5 (Apr. 15, 2008).
SOMAXON Pharmaceuticals Announces Completion of 26-Week Transgenic Mouse Carcinogenicity Study of SILENOR™, Somaxon Pharmaceuticals Press Release, San Diego, CA, p. 1-3 (Jan. 9, 2008).
SOMAXON Pharmaceuticals Announces Data to be Presented at American Psychiatric Association 161st Annual Meeting, Somaxon Pharmaceuticals Press Release, San Diego, CA (May 2, 2008).
SOMAXON Pharmaceuticals Announces Data to be Presented at American Psychiatric Association 161st Annual Meeting, Somaxon Pharmaceuticals Press Release, San Diego, CA, p. 1-7 (May 7, 2008).
SOMAXON Pharmaceuticals Announces FDA Approval of SILENOR® (Doxepin) for the Treatment of Insomnia, Somaxon Pharmaceuticals Press Release, San Diego, CA, p. 1-5 (Mar. 18, 2010).
Somaxon Pharmaceuticals Announces Positive Phase 3 Results with SILENOR™ for theTreatment of Adults with Chronic Insomnia, Somaxon Pharmaceuticals, p. 1-5, (Apr. 10, 2006).
Somaxon Pharmaceuticals Announces Positive Results in a Phase II Dose-Finding Study of Low-dose Doxepin in Adults with Primary Sleep Maintenance Insomnia, Somaxon Pharmaceuticals, p. 1-2, (Jan. 6, 2005).
Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).
SOMAXON Pharmaceuticals Announces Presentation of Phase II SILENOR® Data at the Associated Professional Sleep Societies Annual Meeting, Somaxon Pharmaceuticals, p. 1-2, (Jun. 20, 2006).
SOMAXON Pharmaceuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
SOMAXON Pharmaceuticals Presents Analyses of Silenor Clinical Data at the American Psychiatric Association Annual Meeting, Somaxon Pharmaceuticals Press Release, San Diego, CA, p. 1-6 (May 20, 2009).
SOMAXON Pharmaceuticals Presents Pharmacological Data on Doxepin at the 21st European College of Neuropsychopharmacology Congress, Somaxon Pharmaceuticals Press Release, San Diego, CA, p. 1-3 (Sep. 2, 2008).
SOMAXON Pharmaceuticals Provides Update on New Drug Application for SILENOR® (Doxepin) for the Treatment of Insomnia, Somaxon Pharmaceuticals Press Release, San Diego, CA, p. 1-4 (Apr. 7, 2009).
SOMAXON Pharmaceuticals Provides Update on New Drug Application for SILENOR® for the Treatment of Insomnia, Somaxon Pharmaceuticals Press Release, San Diego, CA, p. 1-3 (Jan. 21, 2010).
SOMAXON Pharmaceuticals Provides Update on Preclinical and Clinical Programs for SILENOR™, Somaxon Pharmaceuticals Press Release, San Diego, CA, p. 1-3 (Sep. 11, 2006).
SOMAXON Pharmaceuticals Provides Update on SILENOR® Development Program for the Treatment of Insomnia, Somaxon Pharmaeuticals, p. 1-5, (Jul. 19, 2006).
SOMAXON Pharmaceuticals Provides Update on SILENOR™ Development Program, Somaxon Pharmaceuticals Press Release, San Diego, CA, p. 1-3 (May 9, 2007).
SOMAXON Pharmaceuticals Provides Update on SILENOR™ Preclinical Program, Somaxon Pharmaceuticals Press Release, San Diego, CA, p. 1-7 (Feb. 13, 2007).
SOMAXON Pharmaceuticals Receives Complete Response Letter from the FDA for SILENOR® (Doxepin), Somaxon Pharmaceuticals Press Release, San Diego, CA, p. 1-3 (Feb. 26, 2009).
SOMAXON Pharmaceuticals Receives Complete Response Letter from the FDA for SILENOR® NDA, Somaxon Pharmaceuticals Press Release, San Diego, CA, p. 1-3 (Dec. 7, 2009).
SOMAXON Pharmaceuticals Resubmits New Drug Application for SILENOR® (Doxepin) for the Treatment of Insomnia, Somaxon Pharmaceuticals Press Release, San Diego, CA, p. 1-4 (Jun. 4, 2009).
SOMAXON Pharmaceuticals Scheduled to Meet with FDA to Discuss Complete Response Letter for SILENOR® NDA, Somaxon Pharmaceuticals Press Release, San Diego, CA (Dec. 17, 2009).
SOMAXON Pharmaceuticals' SILENOR® Data Presented at the 22nd Annual Meeting of the Associated Professional Sleep Societies, Somaxon Pharmaceuticals Press Release, San Diego, CA, p. 1-4 (Jun. 12, 2008).
SOMAXON Pharmaceuticals Submits New Drug Application for SILENOR™ for the Treatment of Insomnia, Somaxon Pharmaceuticals Press Release, San Diego, CA, p. 1-6 (Jan. 31, 2008).
SOMAXON Pharmaceuticals to Present Data at the 22nd Annual Meeting of the Associated Professional Sleep Societies, Somaxon Pharmaceuticals Press Release, San Diego, CA (Jun. 4, 2008).
SOMAXON Pharmaceuticals, Inc. Initiates Phase III Clinical Trials of SILENOR™ in Patients with Insomnia, Somaxon Pharmaceuticals Press Release, San Diego, CA, p. 1-3 (Jun. 9, 2005).
SOMAXON Pharmaceuticals, Inc. Initiates Second Phase III Clinical Trials of SILENOR™ Somaxon Pharmaceuticals Press Release, San Diego, CA (Sep. 20, 2005).
Somaxon Pharmaceuticals' SILENOR™ Demonstrates Positive Results in a Phase 3 Transient Insomnia Clinical Trial, Somaxon Pharmaceuticals, p. 1-5, (Oct. 23, 2006).
Somaxon Pharmaceuticals' SILENOR™ Demonstrates Positive Results in its Third Phase 3 Clinical Trial in Insomnia, Somaxon Pharmaceuticals, p. 1-6, (Nov. 20, 2006).
SOMAXON Pharmaeuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
Somaxon's SILENOR™ Demonstrates Positive Results in Long-Term Phase 3 Clinical Trial in Elderly Patients with Insomnia, Somaxon Pharmaceuticals, p. 1-7, (Dec. 18, 2006).
SOMINEX Caplets. Nightime sleep-aid—Diphenhydramine. GlaxoSmithKline. Consumer Healthcare, L.P. Label. 3 pages.
SOMINEX Oral. Drugs & Medications. WebMD. Web download: Jul. 6, 2010. www.webmd.com/drugs/drug-15470-Sominex+Oral.aspx?drugid=15470&drugname=Sominex+Oral&source=1. p. 1-3.
SONATA (Zaleplon) Capsules. Prescribing Information. King Pharmaceuticals. Feb. 2009. p. 1-15.
SONATA Official FDA information, side effects and uses. Drug Information Online. Drugs.com. Web. Jul. 6, 2010. www.drugs.com/pro/sonata.html. p. 1-22.
Stella et al.—Prodrugs: Challenges and Rewards, Part 1, Biotechnology: Pharmaceutical Aspects, p. 24, 2007.
Stimmel et al., Mirtazapine: An Antidepressant with Noradrenergic and Specific Serotonergic Effects Pharmacotherapy, (1997) 17(1): 10-21.
Summary Basis for approval of ADAPIN (1972) Pursuant to FOIA Request filed in 1981.
Summary Basis for approval of SINEQUAN® (1973) Pursuant to FOIA Request filed in 1973 (sedative, tranquilizer and sleep effects mentioned for example on pp. 50, 54-56, 58-59).
Technical Information/Summary of Drug Characteristics (SPC), Pfizer, p. 1-4, (2004).
Thase, Michael E., Antidepressant Treatment of the Depressed Patient with Insomnia, J. Clin. Psychiatry (1999) 60(Suppl. 17): 28-31.
TYLENOL PM Extra Strength Pain Reliever. Nighttime Sleep Aid. Contains Acetaminophen, Diphenhydramine HCI. 24 Geltabs. Label. 4 pages.

(56) References Cited

OTHER PUBLICATIONS

TYLENOL PM Oral. Drugs & Medications—WebMD. Web download: Jul. 6, 2010. www.webmd.com/drugs/drug-74986-Tylenol+PM+Oral.aspx?drugid=74986&drugname=Tylenol+PM+Oral&source=1. p. 1-3.
Tylenol PM. Extra Strength Pain Reliever. Nighttime Sleep Aid. Contains Acetaminophen, Diphenhydramine HCI. 50 Caplets. Label. 4 pages.
Vincent et al., Use of Human Sleep as a Test of Drug's Psychotropic Action with Doxepin as an example, Bordeaux Medical, No. 10, 2650-51, 2653-54, 2657-57, and 2661, (1971).
Virtanen et al., Radioimmunoassay for doxepin and desmethyldoxepin., Acta Pharmacol Toxicol (Copenh). 47(4):274-8 (1980).
Voshaar et al., Zolpidem is not Superior to Temazepam with Respect to Rebound Insomnia: A Controlled Study. Eur Neuropsychopharmacol. 14(4): 301-306 (2004).
Ward et al., Doxepin plasma levels and therapeutic response in depression: preliminary findings. J Clin Psychopharmacol. 2(2):126-8 (1982).
Ware, Tricyclic Antidepressants in the Treatment of Insomnia, Journal of Clinical Psychiatry, 44 [9, Section 2]: 25-28 (1983).
Wheatley, Prescribing Short-Acting Hypnosedatives: Current Recommendations from a Safety Perspective, Drug Safety 7(2):106-115 (1992).
Wolfe, Antidepressant Withdrawal Reactions. Am Fam Physician. 56(2): 455-462, (1997).
Wyatt et al., Carbon$^{13}$ NMR of Z- and E-Doxepin Hydrochloride. Applied Spectroscopy. 49(4):538-542 (1986).
Yan et al., Stereoselective and simultaneous measurement of cis- and trans-isomers of doxepin and N-desmethyldoxepin in plasma or urine by high-performance liquid chromatography. J Chromatogr B Biomed Sci Appl. 691(1):131-8 (1997).
Yan et al., Stereoselective in vivo and in vitro studies on the metabolism of doxepin and N-desmethyldoxepin. Xenobiotica. 27(12): 1245-1257 (1997).
ZALEPLON Capsules. Drug Information Online. Drugs.com. Web download: Aug. 25, 2009. www.drugs.com/pro/zaleplon.html?printable=1. and Package Label. Augobindo Pharma Ltd. p. 1-23.
Ziegler et al., Doxepin kinetics. Clin Pharmacol Ther. 23(5):573-9 (1978).
Zimmermann et al., "Epidemiology, implications and mechanisms underlying drug-induced weight gain in psychiatric patients" J. Psychiatric Research (2003) 37: 193-220.
Zung, Effect of Antidepressant Drugs on Sleeping and Dreaming, Excerpta Medica Foundation International Congress Series, No. 150, 1824-1826, (1968).
International Search Report and Written Opinion dated Jan. 21, 2008 in PCT/US2007/012107, filed May 18, 2007.
International Preliminary Report on Patentability & Written Opinion dated Nov. 21, 2008 in PCT/US2007/012107, filed May 18, 2007.
International Search Report dated Dec. 10, 2007 in PCT/US2007/016464, filed Jul. 20, 2007.
International Preliminary Report on Patentability & Written Opinion dated Jan. 20, 2009 in PCT/US2007/016464, filed Jul. 20, 2007.
International Search Report dated Jan. 24, 2008 in PCT/US2007/012105, filed May 18, 2007.
International Preliminary Report on Patentability & Written Opinion dated Nov. 21, 2008 in PCT/US2007/012105, filed May 18, 2007.
International Search Report dated Jan. 24, 2008 in PCT/US2007/012106, filed May 18, 2007.
International Preliminary Report on Patentability & Written Opinion dated Nov. 21, 2008 in PCT/US2007/012106, filed May 18, 2007.
International Search Report dated Jun. 17, 2008 in PCT/US2007/080492, filed Oct. 4, 2007.
International Preliminary Report on Patentability & Written Opinion dated Apr. 7, 2009 in PCT/US2007/080492, filed Oct. 4, 2007.
International Search Report dated Aug. 11, 2007 in PCT/US2007/011893, filed May 18, 2007.
International Preliminary Report on Patentability dated Dec. 4, 2008 in PCT/US2007/011893, filed May 18, 2007.
International Search Report dated Mar. 18, 2008 in PCT/US2007/082569, filed Oct. 25, 2007.
Partial International Search Report dated Apr. 8, 2008 in PCT/US2007/082569, filed Oct. 25, 2007.
International Preliminary Report on Patentability dated May 7, 2009 in PCT/US2007/082569, filed Oct. 25, 2007.
International Search Report and Written Opinion dated Jul. 29, 2008 in PCT/US2007/086682, filed Dec. 6, 2007.
International Preliminary Report on Patentability and Written Opinion dated Jun. 18, 2009 in PCT/US2007/086682, filed Dec. 6, 2007.
International Search Report and Written Opinion dated Aug. 13, 2009 in PCT/US2009/042912, filed May 5, 2009.
International Search Report and Written Opinion dated Jan. 19, 2008 in PCT/US2008/060131, filed Apr. 11, 2008.
International Preliminary Report on Patentability dated Oct. 13, 2009 in PCT/US2008/060131, filed Apr. 11, 2008.
Electronic File History of U.S. Appl. No. 11/781,165, filed Jul. 20, 2007 (U.S. Pat. No. 7,915,307, issued Mar. 29, 2011) containing Office Action(s) dated Oct. 14, 2008, Jul. 7, 2009, Sep. 29, 2009, Apr. 6, 2010, Oct. 21, 2010 and Nov. 12, 2010 and Applicant Response(s) filed Apr. 14, 2009, Dec. 4, 2009, Jul. 6, 2010 and Oct. 21, 2010 as of Sep. 14, 2012.
Electronic File History of U.S. Appl. No. 11/804,722, filed May 18, 2007 (Abandoned) containing Office Action(s) dated Jun. 15, 2010, Nov. 8, 2010 and Jun. 2, 2011 and Applicant Response(s) filed Oct. 15, 2010.
Electronic File History of U.S. Appl. No. 11/804,720, filed May 18, 2007 containing Office Action(s) dated Feb. 25, 2009, Nov. 30, 2009, Mar. 17, 2011, Jul. 27, 2011, and Aug. 16, 2011 and Applicant Response(s) filed Aug. 25, 2009, May 27, 2010, Dec. 27, 2010 and May 17, 2011 as of Dec. 16, 2011.
Electronic File History of U.S. Appl. No. 12/022,628, filed Jan. 30, 2008 containing Office Action(s) dated Mar. 6, 2009 and Nov. 20, 2009—abandoned.
Electronic File History of U.S. Appl. No. 12/022,788, filed Jan. 30, 2008 containing Office Action(s) dated Mar. 9, 2009 and Dec. 9, 2009—abandoned.
Electronic File History of U.S. Appl. No. 12/976,866, filed Dec. 27, 2010 (Abandoned) containing Office Action(s) dated Oct. 19, 2011 and Dec. 8, 2011 and Applicants Response filed Sep. 30, 2011.
Electronic File History of U.S. Appl. No. 11/867,595, filed Oct. 4, 2007 containing Office Action(s) dated Oct. 21, 2010, and May 10, 2011 and Applicants Response(s) filed Apr. 20, 2011, Sep. 30, 2011, Nov. 10, 2011 and Jul. 11, 2012 as of Sep. 26, 2012.
Council on Drugs, Evaluation of Doxepin Hydrochloride (Sinequan), JAMA, 215(12): 1967-68 (Mar. 22, 1971).
Pollack et al., The Selective GABA Reuptake Inhibitor Tiagabine for the Treatment of Generalized Anxiety Disorder: Results of a Placebo-Controlled Study, J Clin Psychiatry 66: 1401-1408 (Nov. 2005).
Rodenbeck et al., The sleep-improving effects of doxepin are paralleled by a normalized plasma cortisol secretion in primary insomnia, Psychopharma. 170(4): 423-428 (2003).
BPAI decision issued Dec. 11, 2012 in U.S. Appl. No. 11/804,720, filed May 18, 2007.
Electronic File History of U.S. Appl. No. 12/301,457, filed Apr. 12, 2010 containing Office Action(s) dated Jun. 7, 2012 and Applicants Response(s) filed Apr. 12, 2010 and Nov. 29, 2012 as of Dec. 17, 2012.
Electronic File History of U.S. Appl. No. 12/446,914, filed May 27, 2010 containing Office Action(s) dated Aug. 5, 2011, Jan. 20, 2012, Feb. 17, 2012 and Sep. 5, 2012 and Applicants Response(s) filed May 27, 2010, Jan. 20, 2012, and Aug. 17, 2012 as of Sep. 25, 2012.
Electronic File History of U.S. Appl. No. 13/007,334, filed Jan. 14, 2011 (Abandoned) containing Office Action(s) dated Apr. 17, 2012, as of Sep. 25, 2012.

(56) References Cited

OTHER PUBLICATIONS

Electronic File History of U.S. Appl. No. 12/102,985, filed May 6, 2011 (Abandoned) containing Office Action(s) dated Mar. 16, 2012 and Applicant(s) submissions Dec. 22, 2011 and Sep. 17, 2012 abandoned.
Electronic File History of U.S. Appl. No. 12/101,917, filed Apr. 11, 2008 containing Office Action(s) dated Oct. 21, 2010, May 10, 2011, Jan. 12, 2012 and Nov. 21, 2012 Applicants Response(s) filed Dec. 2, 2008, Dec. 29, 2011 and Jul. 30, 2012 as of Dec. 17, 2012.
Civil Docket of the U.S. District Court, District of Delaware, Case #1:11-cv-00537-RGA-MPT, printed Dec. 21, 2012 involving U.S. Pat. No. 6,211,229 and 7,915,307 of Somaxan Pharmaceuticals, Inc., pp. 1-5.
Office Communications Issued in U.S. Appl. No. 14/045,645, filed Jan. 28, 2015.

* cited by examiner

METHODS OF TREATING INSOMNIA USING A COMBINATION THERAPY OF LOW-DOSE DOXEPIN AND ZOLPIDEM

RELATED APPLICATIONS

This application is a continuation of U.S. patent application Ser. No. 12/517,507, filed Apr. 5, 2012 now abandoned, which is the US National Phase filing under 35 USC 371 of PCT/US2007/086682, filed Dec. 6, 2007, which claims priority to, and incorporates by reference in their entireties, U.S. Patent Application No. 60/873,056, filed Dec. 6, 2006, and U.S. Patent Application No. 60/910,586, filed Apr. 6, 2007, both entitled COMBINATION THERAPY USING LOW-DOSE DOXEPIN FOR THE IMPROVEMENT OF SLEEP.

FIELD OF THE INVENTION

The present invention relates to compositions comprising low-dose doxepin combined with at least one other compound or composition and to methods of treating sleep disorders using these compositions.

BACKGROUND OF THE INVENTION

Sleep is essential for health and quality of life. Insomnia is a growing health problem in the United States. It is believed that more than 30-45 million people suffer from chronic insomnia and up to an additional 70 million people suffer from some form of insomnia each year. Insomnia is a condition characterized by difficulty falling asleep (sleep onset), waking frequently during the night (fragmented sleep), waking too early (premature final awakening), and/or waking up feeling un-refreshed. In the National Sleep Foundation's (NSF) Sleep in America Poll 2005, 42% of survey respondents reported that they awoke frequently during the night, 22% of adults reported waking too early and not being able to return to sleep and 38% reported waking and feeling un-refreshed.

Sleep maintenance difficulty is the most commonly reported symptom in primary care patients with chronic insomnia, and is the most common insomnia complaint in depressed patients, medically ill populations, especially those with pain symptoms, and in the elderly.

Medications commonly used to treat sleep disorders, such as insomnia, include sedative antidepressants, antihistamines, antipsychotics, benzodiazepines, non-benzodiazepine GABA modulators and a recently approved melatonin receptor agonist. Benzodiazepines enhance the activity of gamma amino butyric acid (GABA), the main inhibitory neurotransmitter of the central nervous system, resulting in activation of GABA receptors which favors sleep.

Unfortunately, many of these existing medications have very undesirable side effects, including abnormal thinking and behavioral changes such as decreased inhibition, hallucinations, complex behaviors such as sleep driving, amnesia, anxiety, suicidal thinking; withdrawal symptoms; CNS depressant effects; impaired motor or cognitive performance (particularly in the elderly); bad taste; headaches; parasomnias such as sleep walking; anaphylactic and anaphylactoid reactions; weight gain; or result in rebound insomnia or tolerance.

In addition, existing sleep medications have failed to satisfactorily treat sleep disorders. For example, although benzodiazepines and other GABA modulators, as well as melatonin receptor agonists, promote sleep onset, they have limited effectiveness in promoting a full night's sleep into the $7^{th}$ and $8^{th}$ hours of the night and have no demonstrated benefit in reducing early awakenings.

Embodiments of the present invention relate to the use of doxepin in combination with other drugs to provide safer and improved sleep therapies.

SUMMARY OF THE INVENTION

Embodiments of the present invention generally relate to compounds, compositions and methods for treating sleep disorders using doxepin in combination with one or more other medications. In particular, these combinations surprisingly and unexpectedly have the ability to provide improved sleep, but also can be used with a reduced dosage (e.g., reduced when compared to the normal dosage when used alone) of one or both of doxepin and the one or more other medications while more effectively treating the sleep disorders with fewer adverse side effects. For example, the combinations can avoid or reduce the side effects seen with the therapeutically effective dose of the drug when used alone or when an approved mono treatment dosage is used.

Furthermore, as discussed herein, doxepin is very effective at addressing sleep maintenance aspects of insomnia and at reducing early morning awakenings that can occur in some cases of insomnia. Some embodiments described herein relate to combination compositions comprising doxepin and at least one other medication that is effective for providing sleep onset, as well as methods of using the combination compositions. It should be noted that the combinations can include other sleep maintenance drugs, as well. Preferred sleep onset drugs for the combinations include gamma-aminobutyric acid (GABA) compounds (e.g., modulate GABA activity and/or facilitate GABA transmission), H3 agonists, orexin receptor antagonists, melatonin agonists and galanin agonists.

Thus, some embodiments of the present invention relate to compositions that include doxepin, or a pharmaceutically acceptable salt or prodrug thereof, and one or more of a compound that modulates GABA activity (e.g., enhances the activity and facilitates GABA transmission, a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and the like. In some preferred embodiments, doxepin, doxepin salt or doxepin prodrug can be utilized in a dosage that is the same as the approved dosage for the drug, the clinical test dosage or the dosage used for the drug as a monotherapy for a sleep disorder. In some aspects, the dosage of doxepin can be, for example, between about 0.0001 mg and 49 mg. Preferably the amount of doxepin is between about 0.0001 mg and 20 mg, between about 0.001 mg and 10 mg, more preferably between about 0.01 mg and 9 mg, and still more preferably between about 0.01 mg and 6 mg. In some embodiments, the one or more drugs used in combination with doxepin, including those drugs of the listed categories can be utilized in a dosage that is the same as the approved dosage for the drug, the clinical or literature test dosage of the drug, or the dosage used for the drug as a monotherapy for a sleep disorder. In some aspects, both the doxepin and the one or more combination drugs can be used at a dosage that is the same as or lower than the approved dosage for the drug, the clinical or literature test dosage or the dosage used for the drug as a monotherapy, preferably at a dosage that is lower than when used in their respective monotherapies.

In one embodiment, without being limited thereto, the GABA compound can be, for example, one or more of alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, zolpidem, gabaxadol, vigabatrin, tiagabine, EVT 201 (Evotec Pharmaceuticals) or estazolam. Without being limited thereto, the 5HT2a antagonist may be, for example, one or more of ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), ITI-722 (Intra-Cellular Therapies) or A VE8488 (Sanofi-Aventis, France). In another embodiment, the melatonin agonist can be for example, one or more of melatonin, ramelteon (ROZEREM®, Takeda Pharmaceuticals, Japan), VEC-162 (Vanda Pharmaceuticals, Rockville, Md.), PD-6735 (Phase II Discovery) or agomelatine. The ion channel blocker may be, without limitation, one or more of lamotrigine, gabapentin or pregabalin. The orexin receptor antagonist may be one or more of orexin, a 1,3-biarylurea, SB-334867-a (GlaxoSmithKline, UK), ACT-078573 (Actelion, Switzerland), GW649868 (GlaxoSmithKline) or a benzamide derivative, for example. Without being limited thereto, the serotonin-2 antagonist/reuptake inhibitor (SARI) may be one or more of Org 50081 (Organon-Netherlands), ritanserin, nefazodone, serzone or trazodone. The 5HT1a agonist may be, for example, one or more ofrepinotan, sarizotan, eptapirone, buspirone or MN-305 (MediciNova, San Diego, Calif.). The neurokinin-1 drug can be for example, Casopitant (GlaxoSmithKline). It should be understood that the combination compositions can include mixtures of the combined drugs, as well as two or more separate compositions of the drugs, which individual compositions can be, for example, co-administered together to a patient. Again, in some preferred embodiments the dosages of these drugs can be the same as or lower than the approved dosage for the drug, the clinical or literature test dosage or the dosage used for the drug as a monotherapy.

Some embodiments of the present invention also provide pharmaceutical compositions or formulations that include any of the compositions described above and a pharmaceutically acceptable excipient or diluent.

Some embodiments relate to compositions comprising doxepin, a pharmaceutically acceptable salt or prodrug thereof, and one or more of a compound that promotes sleep onset. The compound that promotes sleep onset can be, for example, a GABA modulator, an H3 agonist, an orexin receptor antagonist, a melatonin agonist a galanin agonist or the like. The composition can include doxepin in an amount of about 0.001 to about 10 mg, for example. The one or more of a compound that promotes sleep onset can be, for example, in a dosage that is the same as the approved prescription dosage for that compound, the same as the clinical trial dosage for the compound, the same as a literature reported dosage for treating a sleep disorder, or the same as the dosage for the compound when used to treat a sleep disorder as a monotherapy. Also, the one or more of a compound that promotes sleep onset can be, for example, in a dosage that is less than the approved prescription dosage for that compound to treat a sleep disorder, less than the clinical trial dosage for the compound for treating a sleep disorder, less than a literature reported dosage for treating a sleep disorder, less than the dosage for the compound when used to treat a sleep disorder as a monotherapy, or less than the monotherapy dosage of the compound required to achieve substantially the same sleep therapy benefit as the compound used in combination with doxepin.

Still some embodiments relate to methods of reducing a side effect of a sleep medication, comprising identifying a patient suffering from a side effect caused by a non-doxepin sleep medication; providing the patient with doxepin in an amount of about 0.0001 to about 10 mg or a pharmaceutically acceptable salt of doxepin, or a prodrug of doxepin; and providing the patient with the non-doxepin sleep medication in a dosage less than the dosage which causes the side effect when the medication is used as sleep therapy alone.

Some embodiments relate to methods of treating a sleep disorder while minimizing side effects of at least one drug in a drug combination, comprising providing at least one non-doxepin sleep drug and at least one doxepin compound, wherein the combination of the at least one non-doxepin sleep drug and the doxepin compound promote a sleep effect that is at least equivalent to the sleep effect of a greater amount of the at least one non-doxepin sleep drug when used without doxepin or when used as a monotherapy for the sleep disorder; and where the doxepin compound is doxepin, a pharmaceutically acceptable salt of doxepin, or a prodrug of doxepin, in an amount of about 0.0001 mg to about 20 mg. For example the sleep effect can be an improvement in a sleep parameter such as time to sleep onset, sleep maintenance time, WASO, WTDS, WTDS, or any other parameter for measuring sleep quality. The side effect can include, for example, one or more of decreased inhibition, hallucinations, complex behaviors such as sleep driving, amnesia, anxiety, suicidal thinking; withdrawal symptoms; CNS depressant effects; impaired motor or cognitive performance; bad taste; headaches; parasomnias such as sleep walking; anaphylactic and anaphylactoid reactions; weight gain; rebound insomnia or tolerance, and the like.

Some embodiments relate to methods of treating a sleep disorder while minimizing side effects of at least one non-doxepin sleep drug, comprising providing at least one non-doxepin sleep drug and a doxepin compound, wherein the combination of the at least one non-doxepin sleep drug and the doxepin compound promote a sleep effect that is at least equivalent to the sleep effect of a greater amount of the at least non-doxepin sleep drug individually or the to the sleep effect of a greater amount of the doxepin compound when used individually to treat the sleep disorder; and where the doxepin compound is doxepin, a pharmaceutically acceptable salt of doxepin, or a prodrug of doxepin, in an amount of about 0.0001 mg to about 20 mg.

Still further embodiments relate to methods of treating a sleep disorder, comprising identifying a patient, wherein said patient is or has been administered a non-doxepin sleep medication at a first dosage (for example to treat a sleep disorder as without the use of doxepin); and providing to said patient the non-doxepin sleep medication at a second dosage and doxepin, a pharmaceutically acceptable salt of doxepin or a prodrug of doxepin; wherein said second dosage of the non-doxepin sleep medication is less than said first dosage. In some aspects, the providing of the second dosage of the non-doxepin medication results in fewer side effects while still providing a beneficial sleep therapy. The sleep medication can be, for example, a GABA modulator, an H3 agonist, an orexin receptor antagonist, a melatonin agonist and a galanin agonist.

Still some embodiments of the present invention relate to methods of treating insomnia, for example, including identifying an individual in need of such treatment, and administering any of the compositions described above to the individual. In one embodiment, the doxepin or pharmaceutically acceptable salt or prodrug thereof can be administered at any dosage described herein, for example, a dosage of 0.01 to 49 mg. In another embodiment, the doxepin or pharmaceutically acceptable salt or prodrug thereof is administered at a dosage of 0.1 to 20 mg. In yet another embodiment, the doxepin or pharmaceutically acceptable salt or prodrug thereof is administered at a dosage of about 0.5 to 10 mg. In still another embodiment, the doxepin or pharmaceutically acceptable salt or prodrug thereof is administered at a dosage of about 1 to 6 mg.

Another embodiment of the present invention relates to methods of treating insomnia, comprising identifying an individual in need of such treatment, and administering any of the pharmaceutical formulations described above to the individual. In one embodiment, the doxepin or pharmaceutically acceptable salt or prodrug thereof can be administered at any dosage described herein.

The present invention also provides methods of enhancing sleep maintenance, comprising identifying an individual in need of such enhancement, and administering any of the compositions described above or elsewhere herein to the individual. In one embodiment, the doxepin or pharmaceutically acceptable salt or prodrug thereof can be administered at any dosage described herein.

Another embodiment of the invention relates to method of enhancing sleep maintenance and preventing early awakenings, comprising identifying an individual in need of such enhancement, and administering any of the pharmaceutical formulations described above or elsewhere herein to the individual. In one embodiment, the doxepin or pharmaceutically acceptable salt or prodrug thereof can be administered at any dosage described herein. Doxepin or a pharmaceutically acceptable salt or prodrug thereof may be administered with a drug disclosed herein, such as a sleep maintenance drug, a gamma-aminobutyric acid (GABA) compound, an H3 agonist, an orexin receptor antagonist, an melatonin agonist or a galanin agonist, wherein the drug is administered at substantially the same approved dosage for the drug, the same as the clinical or literature test dosage of the drug, the same dosage used for the drug as a monotherapy for a sleep disorder, or lower than any of those dosages for the drug.

The present invention also relates to methods for selecting a sleep drug therapy for a patient from among available therapies, comprising evaluating whether the patient is in need of both sleep onset and sleep maintenance therapy, and if so; selecting for the patient any of the drug combinations described above. In some aspects the methods can also comprise evaluating whether the patient is in need of a drug to minimize early awakenings, and if so, selecting for any of the combinations described herein.

Another embodiment of the invention relates to methods for treating insomnia, comprising administering or coadministering to an insomnia patient effective amounts of doxepin or a pharmaceutically acceptable salt or prodrug thereof, and one or more of a compound that modulates gamma-aminobutyric acid (GABA) activity (e.g., enhances the activity) and facilitates GABA transmission, a GABA-B agonist, a 5-HT modulator (e.g., a 5-HT1a agonist, a 5-HT2a antagonist, a 5-HT2a inverse agonist, etc.), a melatonin agonist (including melatonin), an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and the like. In some aspects the methods can further include informing the patient to take the doxepin and said one or more compounds with or without food, or with or without fatty food, preferably without food or without fatty food.

Some embodiments of the present invention relate to methods for reducing a risk of drug abuse, comprising identifying a patient in need of sleep drug therapy and in need of avoidance of drugs with potential for abuse; and administering to the patient any of the drug combinations described above. In one embodiment, the drug combination can be doxepin or a pharmaceutically acceptable salt or prodrug thereof, and a compound that enhances GABA activity. The compound that enhances GABA activity may be alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, zolpidem, gabaxadol, vigabatrin, EVT 201 (Evotec Pharmaceuticals), tiagabine or estazolam.

Another embodiment of the invention relates to methods for treating insomnia, comprising administering to a patient in need thereof an effective amount of doxepin or a pharmaceutically acceptable salt or prodrug thereof, in combination with an effective amount of a 5HT2a receptor antagonist or reverse agonist. The 5HT2a antagonist may be for example, one or more of ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), ITI-722 (Intra-Cellular Therapies) or AVE8488 (Sanofi-Aventis, France).

Further embodiments of the present invention relate to methods for treating insomnia, comprising administering to a patient in need thereof an effective amount of doxepin or a pharmaceutically acceptable salt or prodrug thereof, in combination with an effective amount of a sleep-onset-enhancing drug. In one embodiment, the sleep-onset-enhancing drug can be one or more of a GABA compound (e.g., modulate GABA activity and facilitate GABA transmission), H3 agonists, orexin receptor antagonists, melatonin agonists and galanin agonists. The sleep-onset-enhancing drug may be ramelteon, eszopiclone, zolpidem tartrate or zaleplon. In some aspects the methods can include a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like.

DETAILED DESCRIPTION OF THE INVENTION

Sleep disorders are a growing health problem. Unfortunately, as mentioned above, many sleep drugs fail to satisfactorily treat all or certain aspects of sleep disorders. For example, some drugs may be effective at promoting sleep onset, while others may promote sleep maintenance, or visa versa. Further, many of the medications that may have some therapeutic efficacy against aspects of sleep disorders cause very undesirable side effects. Side effects caused by sleep medications include abnormal thinking and behavioral changes such as decreased inhibition, hallucinations, complex behaviors such as sleep driving, amnesia, anxiety, suicidal thinking; withdrawal symptoms; CNS depressant effects; impaired motor or cognitive performance (particularly in the elderly); bad taste; headaches; parasomnias such as sleep walking; anaphylactic and anaphylactoid reactions; weight gain; rebound insomnia or tolerance.

Embodiments of the invention relate to compositions and methods for improved treatments of sleep disorders utilizing doxepin in combination with at least one other sleep medication. Also, some embodiments relate to methods of treating sleep disorders with combinations of doxepin and other sleep medications, while avoiding or reducing the side effects that a patient experiences. Surprisingly, the combinations and methods can result in an unexpected synergy both in terms of their therapeutic effect on sleep and/or in terms of the reduced side effects.

In some aspects the methods and compositions permit the use of a reduced dosage of one or both of the doxepin and the other medication(s), while still providing effective treatment (ie. providing sleep onset, sleep maintenance, and preventing early awakenings) of the sleep disorder, including in some aspects, improved treatment compared to the use of either doxepin or the combination medication(s) alone.

A number of existing sleep drugs can promote sleep onset, but are less effective for promoting sleep maintenance, promoting fewer awakenings during the night or delaying the final awakening in the morning. Doxepin is an all around effective sleep medication, but is particularly effective at promoting sleep maintenance throughout the night and in preventing early morning awakenings. Some preferred embodiments relate to methods and compositions that combine doxepin with one or more drugs that are effective at promoting sleep onset. The combined drugs can provide greater than expected sleep benefit, in some cases, even when using a lower dose of one or more of the drugs. The lower dose can be a dosage that is lower compared to the approved dosage of the drug(s), the clinical tested or literature reported dosage for sleep therapy for the drug(s), the dosage of the drug(s) used in a mono sleep therapy, or the dosage required to provide the patient with an approximately similar sleep benefit (time to sleep onset, total sleep time, sleep efficiency, wake time after sleep onset, etc.). Examples of some preferred sleep onset medications include gamma-aminobutyric acid (GABA) compounds (e.g., modulate GABA activity and/or facilitate GABA transmission), H3 agonists, orexin receptor antagonists, melatonin agonists and galanin agonists.

In some embodiments, the combined drugs can provide substantially the same sleep benefit as expected when using a higher dosage of one or both of the drugs, but provide fewer side effects than occur at such a higher dosage. In some embodiments, the combined drugs can provide surprisingly improved sleep benefit compared to when using a higher dosage of one or both of the drugs, and provide fewer side effects than occur at such a higher dosages.

Some embodiments relate to the use doxepin in combination with one or more drugs that promote sleep maintenance and/or one or more drugs that promote a reduced number of awakenings during the night. Still further embodiments relate to the use of doxepin in combination with a drug or drugs that promote two or more of sleep onset, sleep maintenance, or reduced awakenings. Again, due to the unexpected therapeutic efficacy, lower dosages of one or all compounds can be used.

Embodiments of the present invention generally relate to methods of using low dosages of doxepin, doxepin prodrugs, and pharmaceutically acceptable salts of the same, in combination with any one or more compounds that enhance sleep, for example, sleep onset, sleep maintenance or the prevention of early awakenings.

Examples of compounds that can be used in the combinations include, but are not limited to, GABA compounds (e.g., modulate GABA activity and facilitate GABA transmission), melatonin receptor agonists, 5-HT modulators (e.g., 5-HT1A agonists, 5-HT2A receptor antagonists or inverse agonists, etc.), serotonin-2 antagonists/reuptake inhibitors (SARIs), ion channel modulators, H3 agonists, orexin receptor antagonists, noradrenergic antagonists, galanin agonists, CRH antagonists, Gabaxodol, other GABA-A direct antagonists, GABA-B direct agonists GABA reuptake inhibitors, growth hormone and growth hormone agonists, estrogen and estrogen agonists, neurokinin-1 (NK-1) drugs, and the like. Gabaxodol and GABA-A direct agonists differ in that gabaxodol is extrasynaptic.

In some embodiments, one or more compounds described herein (e.g., a compound that enhances sleep) and a doxepin-related compound may be provided in relative ratios equal to about 0.1:99.9, about 0.5:99.5, about 1:99, about 5:95, about 10:90, about 20:80, about 30:70, about 40:60, about 50:50, about 60:40, about 70:30, about 80:20, about 90:10, about 95:5, about 99:1, about 99.5:0.5, or about 99.1:0.1.

In some embodiments, one or more compounds that enhance sleep may be provided in a first compound dosage that is about 1%, about 5%, about 10%, about 20%, about 30%, about 40%, about 50%, about 60%, about 70%, about 80%, about 90%, about 95%, or about 99% a second compound dosage. The second compound dosage is defined as a dosage that is: a dosage that is an approved prescription dosage for the one or more compounds, a clinical trial dosage for the one or more compounds, a literature-reported dosage of the one or more compounds for treating a sleep disorder, a dosage of the one or more compounds used to treat a sleep disorder as a monotherapy, a dosage of the one or more compounds used to treat a sleep disorder when doxepin is not also used to treat the sleep disorder, or a dosage of the one or more compounds required to achieve substantially the same sleep therapy benefit as the one or more compounds used in combination with doxepin.

In some embodiments, a doxepin-related compound may be provided in a first doxepin dosage that is about 1%, about 5%, about 10%, about 20%, about 30%, about 40%, about 50%, about 60%, about 70%, about 80%, about 90%, about 95%, or about 99% a second doxepin dosage. The second doxepin dosage is defined as a dosage that is: a dosage that is an approved prescription dosage for the doxepin-related compound, a clinical trial dosage for the doxepin-related compound, a literature-reported dosage of the doxepin-related compound, a dosage of the doxepin-related compound used to treat a sleep disorder as a monotherapy, a dosage of the doxepin-related compound used to treat a sleep disorder when other sleep-enhancing compounds are not used to treat the sleep disorder, or a dosage of the doxepin-related compound required to achieve substantially the same sleep therapy benefit as the one or more doxepin-related compound used in combination with one or more sleep-enhancing compounds.

In some embodiments, the combined dosage of the first compound dosage and the first doxepin dosage is less than about 100%, less than about 90%, less than about 80%, less than about 70%, less than about 60%, less than about 50%, less than about 40%, less than about 30%, less than about 20%, or less than about 10% the combined reference dosage of the second compound dosage and the second doxepin dosage. For example, the one or more compounds that enhance sleep may act synergistically. In one instance, the sleep-enhancing compound(s) are primarily effective at treating onset insomnia, while the doxepin-related compound is primarily effective at treating maintenance insomnia. However, the combination drug may include reduced dosages of the sleep-enhancing compound(s) and/or the doxepin-related compound, due to synergistic effects of treating one or both types of insomnia. In some embodiments, the sleep-enhancing compound is provided at a dosage that is a first percentage of the second compound dosage, and the doxepin-related compound is provided at a dosage that is a second percentage of the second doxepin dosage, wherein the combination of the first percentage and the second percentage is less than about 100%, less than about 90%, less than about 80%, less than about 70%, less than about 60%, less than about 50%, less than about 40%, less than about 30%, less than about 20%, or less than about 10%.

Doxepin is a tricyclic compound approved for the treatment of depression and anxiety.

It is contemplated that doxepin for use in the methods described herein can be obtained from any suitable source or made by any suitable method. As mentioned, doxepin is approved and available for the treatment of depression and anxiety. It is generally administered at a daily dose of 75-300 milligrams but, in patients with very mild symptomatology or emotional symptoms accompanying organic disease, lower doses of 25-50 mg/day have been found to be effective Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1—Frazione, Mairano, Italy), or from Dipharma S.p.A. (20021 Baranzate di Bollate, Milano, Italy). Also, doxepin is commercially available from PharmacyRx (NZ) (2820 $1^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 10 mg/ml liquid concentrate from CVS Online Pharmacy Store (CVS.com).

Furthermore, doxepin (11-(3-dimethylaminopropylidene)-6,11-dihydrodibenzo(b,e)oxepin) can be prepared according to the method taught in U.S. Pat. No. 3,438,981, which is incorporated herein by reference in its entirety. An example preparation is described below in Example 1.

Doxepin, unlike most FDA approved products for the treatment of insomnia, is not a Schedule IV controlled substance. U.S. Pat. Nos. 5,502,047 and 6,211,229, the entire contents of which are incorporated herein by reference, describe the use of doxepin for the treatment chronic and non-chronic (e.g., transient/short term) insomnias at dosages far below those used to treat depression.

As mentioned above, some embodiments relate to methods of using doxepin pharmaceutically acceptable salts of doxepin, and/or prodrugs of doxepin to treat a patient suffering from a sleep disorder such as insomnia, by administering a dosage of the "doxpein compound(s)," including a low dosage of any of the above-referenced doxepin compounds in combination with one or more of the compounds described herein.

Definitions

The term "insomnia" generally refers to sleep problems characterized by difficulty falling asleep, wakings during the night, or waking up earlier than desired ("early awakenings"). Examples of insomnia include chronic and non-chronic insomnias. Transient and short term insomnia are examples of non-chronic insomnias. Also, sleep onset insomnia and sleep maintenance insomnia are examples of insomnia conditions that can be chronic or non-chronic in nature and duration.

As used herein, the term "transient insomnia" is an insomnia that is present for one to several days, and is less than one week in duration. Short term insomnia is insomnia of one to three or four weeks in duration.

"Chronic insomnia" is typically accepted to involve episodes greater than three (3) or four (4) weeks in duration.

"Onset insomnia" refers to difficulty in falling asleep.

"Maintenance insomnia" refers to difficulty in maintaining uninterrupted sleep.

It is well known that the sleep deprivation resulting from such insomnia adversely affects cognition, safety and quality of life. Even in otherwise healthy young people, sleep deprivation has been associated, for example, with changes in body physiology such as changes in thyroid function, changes in glucose metabolism and insulin resistance.

As used herein, the term "sedative tolerance" refers to a decreased response to a repeated drug dose which requires increasing amounts to produce the same effect. Tolerance is usually manifested by a decreased duration or magnitude of sedation. Thus, the patient requires larger doses to produce the sedative effects. In contrast, sedative drugs which avoid sedative tolerance achieve sustained efficacy over periods of prolonged or long term use, for example during treatment of chronic sleep disorders.

The term "rebound insomnia" refers to the common occurrence that a person may have more trouble sleeping the first few nights after a sedative medicine is stopped than before starting the medicine. After more than a few days' use, discontinuing a hypnotic can make the original sleep problem worse and increase anxiety. Rebound insomnia may be measured as the mean change in mean wake time after sleep onset (WASO) from baseline to the first night of discontinuation.

The term "early awakenings" refers to final awakenings that occur during what would normally be the last hours of sleep, particularly in the last hour of a sleep period for an individual.

The term "residual next day sedation" refers to the continued sedative effect of a drug the day after it is administered.

The term "administer" and its variants contemplate both self-administration (by the patient) and administration by a third party.

The term "coadminister" and its variants contemplates administering two or more drugs so that their pharmacological effects are substantially simultaneously present in the patient. Thus, one drug can be administered before the other, or one drug can be administered in multiple doses while the other is administered in a single dose. It also contemplates administering the drugs in a physically mixed composition, or administering them simultaneously without mixing outside the body. It further covers administering two or more drugs by different routes of administration, as well as administering the two or more drugs that have different delivery profiles or mechanisms, such as buccal, sublingual, sustained or controlled release, inhalation, transdermal patch, and the like.

As used herein, "doxepin-related compounds" means doxepin, or a pharmaceutically acceptable salt or prodrug thereof.

The term "prodrug" refers to an agent that is converted into the active drug in vivo. Prodrugs are often useful because, in some situations, they may be easier to administer than the active drug. They may, for instance, be bioavailable by oral administration whereas the active drug is not. The prodrug may also have improved solubility in pharmaceutical compositions over the active drug. An example, without limitation, of a prodrug would be a compound of the present invention which is administered as an ester (the "prodrug") to facilitate entry into systemic circulation. A further example of a prodrug might be a short peptide (polyamino-acid) bonded to an acid group where the peptide is metabolized to reveal the active moiety.

The term "pharmaceutically acceptable salt" refers to an ionic form of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like. Pharmaceutically acceptable salts are more fully described below.

The term "low-dose" refers to a dose of 0.0001 to 49 mg, preferably 0.001 to 20 mg, more preferably 0.01 to 10 mg, also 0.1 to about 8 mg, and even more preferably 0.5 or 1 to about 6 mg. The term "low dose" can also refer to a daily dose range of between about 0.0001 and 6 milligrams. In some embodiments, low dosages can be about 1, 2, 3, 4, 5 or 6 milligrams. These dosages have reduced side effects, are surprisingly effective, and have a relatively rapid onset. In one embodiment, an initial daily dosage of about 1 milligram can be given. If the desired improvement in sleep is not achieved, then the dosage may be incrementally increased until the desired dosage is achieved or until a maximum desired dosage is reached which can be, for example, 2 milligrams, 3 milligrams, 4 milligrams, 5 milligrams or 6 milligrams. It should be noted that other dosages of a doxepin-related compound can be used in the embodiments described herein. For example, the dosage can be about 0.001 to about 20 milligrams, for example.

Compounds which enhance GABA activity for use in the compositions and methods of the present invention include, but are not limited to, alprazolam, bromazepam, chlorodiazepoxide, clobazam, clonazepam, clorazepate, diazepam, flunitrazepam, flurazepam, lorazepam, midazolam, nitrazepam, oxazepam, temazepam, triazolam, zolpidem, zaleplon, zopiclone, eszopiclone, gabaxadol, estazolam (Prosom) vigabatrin, tiagabine, EVT 201 (Evotec Pharmaceuticals) and indiplon.

Melatonin receptor agonists for use in the compositions and methods of the present invention include, but are not limited to, melatonin (e.g., Circadin®), ramelteon (ROZEREM®, Takeda Pharmaceuticals, Japan), agomelatine, PD-6735 (Phase II Discovery) and VEC-162 (Vanda Pharmaceuticals, Rockville, Md.). Preferred melatonin receptor agonists are those that are selective for $MT_1$ and/or $MT_2$ receptors, in comparison to $MT_3$ receptors.

5-HT2a receptor antagonists preferably include, but are not limited to, any sleep-enhancing 5-HT2a antagonist or reverse agonist, which in particular embodiments may include eplivanserin (Sanofi-Aventis, France), volinanserin (Sanofi-Aventis, France), ketanserin, risperidone, pruvanserin (Eli Lilly), HY10275 (Eli Lilly), MDL100907 (Sanofi-Aventis, France), APD125 (Arena Pharmaceuticals, San Diego, Calif.), ITI-722 (Intra-Cellular Therapies) or AVE 8488 (Sanofi-Aventis, France).

5-HT1a receptor agonists preferably include, but are not limited to, repinotan, sarizotan, eptapirone, buspirone and MN-305 (MediciNova, San Diego, Calif.).

Serotonin-2 antagonists/reuptake inhibitors (SARIs) include, but are not limited to, Org 50081 (Organon, The Netherlands), ritanserin, nefazodone, serzone and trazodone.

Orexin receptor antagonists include, but are not limited to, 1,3-biarylureas, SB-334867-A (GlaxoSmithKline, UK), GW649868 (GlaxoSmithKline), ACT-078573 (Actelion, Switzerland) and benzamide derivatives, such as those disclosed in U.S. Pat. No. 7,078,565, the contents of which are incorporated herein by reference.

GABA-B agonists include, but are not limited to, (−)baclofen (β-(4-chloro-phenyl)-γ-aminobutyric acid) ("Baclofen")

Other drugs that may be combined with doxepin include gabapentinoids (alpha2 delta ligands), neurokinin-1 drugs (casopitant (GlaxoSmithKline), histamine antagonist compounds (HY10275 Eli Lilly) and ion channel modulators (e.g., gabapentin, pregabalin, lamotrigine).

It should be understood that in some embodiments, one or more compounds from the classes mentioned herein, including the drugs that are specifically mentioned, can be specifically excluded from one or more embodiments of the embodiments described herein. Thus, it is contemplated that one or more of the drugs alone in any combination or number can be specifically excluded from certain embodiments.

Obtaining and Method of Making Doxepin Compounds

It is contemplated that doxepin for use in the methods described herein can be obtained from any suitable source or made by any suitable method. As mentioned, doxepin is approved and available in high doses (generally 75-300 milligrams) for the treatment of depression and anxiety. Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1—Frazione, Mairano, Italy), or from Dipharma S.p.A. (20021 Baranzate di Bollate, Milano, Italy). Also, doxepin is commercially available from PharmacyRx (NZ) (2820 1$^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 10 mg/ml liquid concentrate from CVS Online Pharmacy Store (CVS.com).

Also, doxepin (11-(3-dimethylaminopropylidene)-6,11-dihydrodibenzo (b,e)oxepin) can be prepared according to the method taught in U.S. Pat. No. 3,438,981, which is incorporated herein by reference in its entirety. An example preparation is described below in Example 1. As another illustration, doxepin can be prepared from 11-[3-(Dimethylamino)propyl]-6,11-dihydrodibenzo[b,e]oxepin-11-ol as taught in U.S. Pat. No. 3,420,851, which is incorporated herein by reference in its entirety.

As mentioned above, the methods and other embodiments described herein can utilize any suitable pharmaceutically acceptable salt or prodrug of doxepin. The substitution or use in combination of salts and prodrugs is specifically contemplated in the embodiments described herein. The pharmaceutically acceptable salts and prodrugs can be made by any suitable method. The acids that may be used to prepare pharmaceutically acceptable acid addition salts are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, disylate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "prodrug" refers to a chemical entity that is rapidly transformed in vivo to yield an active entity, for example, such as by hydrolysis in blood or inside tissues, for example. Examples of prodrug groups can be found in, for example, T. Higuchi and V. Stella, in "Pro-drugs as Novel Delivery Systems," Vol. 14, A.C.S. Symposium Series, American Chemical Society (1975); H. Bundgaard, "Design of Prodrugs," Elsevier Science, 1985; and "Bioreversible Carriers in Drug Design: Theory and Application," edited by E. B. Roche, Pergamon Press: New York, 14-21 (1987), each of which is hereby incorporated by reference in its entirety.

Methods of Using Doxepin

Embodiments relate to methods for improving sleep in a patient in need thereof, for example, by administering a doxepin compound and at least one other sleep enhancing medication. The sleep enhancing medication can be, for example, a sleep-onset or maintenance enhancing drug, including a compound from those classes listed above and elsewhere herein e.g., a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SA-RIs), a noradrenergic antagonist, a CRH antagonist, human growth hormone, a growth hormone agonist, estrogen, an estrogen agonist, a neurokinin-1 drug, and the like.

Some embodiments relate to methods of reducing sleep drug side effects in a patient by administering a doxepin compound in combination with one or more sleep drugs in a dosage sufficient to reduce the side effects normally associated with the non-doxepin sleep drug(s). In some aspects, the combination promotes sleep therapy that is at least equivalent to the sleep therapy by the non-doxepin drug(s) when used alone in a greater amount, even though less of the non-doxepin drug is used in the combination.

As mentioned above and elsewhere, the methods described herein can be used to treat individuals suffering from a sleep disorder, such as insomnia. The individual can suffer from a chronic insomnia or a non-chronic insomnia. For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication, for example. The non-chronic insomnia can be, for example, short term insomnia or transient insomnia. The chronic or non-chronic insomnia can be a primary insomnia or an insomnia that is secondary or attributable to another condition, for example a disease such as depression or chronic fatigue syndrome. In some aspects, the patient can be one that is not suffering from an insomnia that is a component of a disease, or a patient can be treated that is otherwise healthy. In some embodiments, the patient can be one that suffers from or is at risk of suffering from drug abuse and/or alcoholism. In some embodiments, the patient can be taking a narcotic medication. As previously mentioned, the chronic or non-chronic insomnia can be a primary insomnia, that is, one that is not attributable to another mental disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-wake system. In some aspects the insomnia can be non-chronic, or of short duration (e.g., less than 3-4 weeks). Examples of causes of such insomnia may be extrinsic or intrinsic and include, but are not limited to environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder. In some aspects, the methods can occur without the untoward side effects of unwanted weight gain, rebound insomnia, or sedative tolerance.

It should be noted that in some aspects, the methods can specifically exclude one or more of any of the sleep disorders described in the previous paragraph or elsewhere herein. For example, without being limited thereto, in some aspects the methods can specifically exclude treating a chronic insomnia. As another example, without being limited thereto, in some aspects the methods can specifically exclude treating an insomnia that is attributable to a condition such as depression, anxiety or chronic fatigue.

In one embodiment, the doxepin, pharmaceutically acceptable salt or prodrug and at least one other compound that enhances or facilitates sleep (e.g., accelerates sleep onset or enhances sleep maintenance), can be administered separately (in two distinct formulations or dosage forms). In various embodiments, the two or more components can be administered at the same time, the doxepin component can be administered prior to the compound that enhances sleep, or vice versa. In another embodiment, the two compounds can be presented in a single formulation (e.g., are present in the same capsule or tablet, such as a bilayer tablet) and are therefore simultaneously coadministered. In some such cases, the combination can be in a fixed ratio combination. Other types of coadministration are expressly contemplated, including administering the doxepin or related drug before the other drug (e.g., 10, 20, 30, 40, 50 or 60 minutes before), administering the doxepin or related drug after the other drug (e.g., 10, 20, or 30 minutes after), administering one drug in a sustained or controlled release form but not the other, administering one by one route of administration and the other by a different route.

One advantage of many of these drug combinations is the ability to treat a particular subset of insomnia patients that has not previously been adequately treated. For example, these patients include those patients that are in need of both rapid sleep onset and sleep maintenance, including maintenance of sleep into the seventh or eighth hour of the night without early awakenings. Also, many of the combinations work unexpectedly well or synergistically. Thus, the methods contemplated herein include methods for providing sleep therapy to a patient, including evaluating whether the patient is in need of both enhanced sleep onset at the beginning of a desired sleep period, and also in need of sleep maintenance at the end of a desired sleep period, and if so, coadministering to the patient the combination therapy disclosed herein, e.g., effective doses of both a doxepin compound and a sleep-onset-enhancing compound. Also contemplated is selecting the presently-disclosed sleep therapy drug combination from available therapies for patients in need of both sleep onset and sleep maintenance therapy. A sleep therapy drug combination disclosed herein may be used to treat patient suffering from early awakenings.

In one embodiment, the patient can be advised to take the drug combination at bedtime. In another, the patient can be advised to take the drug combination with or without food. A food effect has not heretofore been reported for doxepin. In prescribing or administering a combination of doxepin and a melatonin agonist, such as ramelteon, to a patient, one may further advise the patient (verbally or in writing) that the combination should be taken orally, without food, for example, within 30 minutes of bedtime, and not with or immediately after eating, particularly when the food is fatty food. The patient may further be informed orally or in writing that $T_{max}$ for the combination therapy will be delayed if taken with food.

Another aspect of the present disclosure is the relative safety of the doxepin-related component of the combination. Combinations that include a doxepin-related component and a non-scheduled agent such as melatonin or a melatonin agonist can have an increased safety profile and a reduced risk of abuse, when both ingredients are non-scheduled drugs in the U.S. Thus, some of the contemplated methods include a method for providing insomnia drug therapy for a patient, by evaluating whether the patient should avoid therapies with significant potential for abuse, and if so, administering a doxepin-related drug in combination with, for example, a melatonin agonist. Also contemplated is selecting that drug therapy from available drug therapies based on the desire or need to avoid potential for abuse or to avoid or reduce side effects. In some embodiments, a decreased amount of the combination drug or drugs can be used due to the combined effects of the combination. Decreased amount can mean, for example, an amount less than what would be used when using the drug or drugs alone or not combined.

Combinations that include a doxepin-related component and a non-scheduled or a scheduled agent such as a GABA modulator can have an increased safety profile. For example, by administering a doxepin-related component in combination with the scheduled agent, a lower dosage of the scheduled agent may have substantially the same efficacy of a higher dosage of the scheduled agent administered without the doxepin-related component. Thus, side effects associated with the scheduled agent may be reduced by administering the drug combination comprising a decreased amount of the scheduled agent.

The drug combinations disclosed herein have surprising efficacy, even in low doses, and also can allow a full 7 or 8 hours of sleep, without significant next-day sedation. It is believed that these combinations are surprisingly complementary, or even synergistic, filling a long-felt need for a sleep drug that is safe, provides rapid sleep onset, maintains sleep throughout the night for a full 7 or 8 hour sleep cycle, reduces the incidence of early awakenings and allows normal activity the next day without hangover or unsafe levels of sedation.

Also, some embodiments relate to the use of doxepin prodrugs or salts of the same in combination with other insomnia or sleep medications. For example, the methods can include the use of one or more of a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like. In some aspects, doxepin prodrugs or salts thereof in combination with another sleep medication, including those listed above and elsewhere herein, can be administered to a patient without untoward side effects including, but not limited to, decreased inhibition, hallucinations, complex behaviors such as sleep driving, amnesia, anxiety, suicidal thinking; withdrawal symptoms; CNS depressant effects; impaired motor or cognitive performance (particularly in the elderly); bad taste; headaches; parasomnias such as sleep walking; anaphylactic and anaphylactoid reactions; weight gain; or rebound insomnia or tolerance.

Some non-limiting examples of specific drugs and dosages that can be used in combination with a doxepin-related compound are described in the following paragraphs.

Ramelteon ((S)—N-[2-(1,6,7,8-tetrahydro-2 H-indeno-[5,4-b]furan-8-yl)ethyl]propionamide) can be used in any dosage, but preferably can be used in a dosage of about 0.5 milligrams to about 20 milligrams. More preferably, about 4, 8 or 16 milligrams can be used, for example. Even more preferably, the dosage of Ramelteon can be less than about 4 mg, about 8 mg, or about 16 mg, for example between about 0.001 and about 3.9 mg.

Eszopiclone also can be used in any suitable dosage. For example, the dosage can be about 0.1 to about 10 milligrams. Preferably, as an example, the dosage can be about 1, 2, or 3 milligrams. Even more preferably, the dosage of Eszopiclone can be less than about 1 mg, about 2 mg, or about 3 mg, for example between about 0.001 and about 0.9 mg.

Zolpidem (N,N,6-trimethyl-2-p-tolylimidazo[1,2-a] pyridine-3-acetamide L-(+)-tartrate (2:1)) also can be used in any suitable dosage. For example, the dosage can be about 0.1 to about 20 milligrams. Preferably, as an example, the dosage can be about 6.25-milligrams, about 12.5 milligrams or a dosage that is a factor thereof, for example. Even more preferably, the dosage of zolpidem can be less than about 6.25 mg or about 12.5 mg, for example between about 0.0001 and about 5, or between about 0.0001 and about 6 mg. The dosage may be between about 0.001 and about 19.9 milligrams, about 0.001 and about 12.4 milligrams, about 0.001 and about 9.9 milligrams, about 0.001 and about 6.24 milligrams, or about 0.001 and about 4.9 milligrams. It is worth noting that zolpidem (not just zolpidem but all the GABAs) is known to have various undesirable side effects. Use of the low doses described herein when in combination with a doxepin compound provides efficacy as a sleep medication with reduced side effects.

Furthermore, zaleplon (N-[3-(3-cyantopryazolo[1,5-a]pyrimidin-7-yl)phenyl]-N-ethylacetamide) can be used in any suitable dosage. For example, the dosage can be between about 0.1 and about 20 milligrams, about 0.001 and about 19.9 milligrams, about 0.001 and about 12.4 milligrams, about 0.001 and about 9.9 milligrams, about 0.001 and about 6.24 milligrams, or about 0.001 and about 4.9 milligrams. Preferably, as an example, the dosage can be about 5, about 10 or about 20 milligrams, for example. Even more preferably, the dosage of zaleplon can be less than 5 mg, 10 mg, or 20 mg, for example between about 0.01 and 4.9 mg.

Gabaxadol (7-tetra hydroisoxazolo[5,4-c]pyridin-3-ol) can be used in any suitable dosage. For example, the dosage can be about 0.1 to about 40 milligrams. Preferably, as an example, the dosage can be between about 0.5 and about 20 milligrams, about 10 and about 15 milligrams, about 0.001 and about 39.9 milligrams, about 0.001 and about 19.9 milligrams, about 0.001 and about 12.4 milligrams, about 0.001 and about 9.9 milligrams, about 0.001 and about 6.24 milligrams, or about 0.001 and about 4.9 milligrams for example.

VEC-162 can be used in any suitable dosage. For example, the dosage can be about 0.1 to about 150 milligrams. Preferably, as an example, the dosage can be about 10, about 20, about 50 or about 100 milligrams, for example. The dosage can be between about 0.001 and about 149.9 milligrams, about 0.001 and about 99.9 milligrams, about 0.001 and about 49.9 milligrams, about 0.001 and about 19.9 milligrams, or about 0.001 and about 9.9 milligrams. Even more preferably, the dosage of VEC-162 can be about 0.001 to about 9 mg.

Indiplon (N-methyl-N-[3-[3-(2-thienylcarbonyl)-pyrazolo[1,5-]pyrimidin-7-yl]phenyl]acetamide) can be used in any suitable dosage. For example, the dosage can be about 0.1 to about 10 milligrams. Preferably, as an example, the dosage can be about 5 or about 10 milligrams, for example. The dosage can be between about 0.001 and about 9.9 milligrams or about 0.001 and about 4.9 milligrams. Even more preferably, the dosage of indiplon can be about 0.001 to about 4.9 mg.

MDL 100907 (Sanofi-Aventis) can be used in any suitable dosage. For example, the dosage can be about 0.5 to about 100 milligrams, preferably from about 1 to about 50 milligrams. The dosage can between about 0.001 and about 99.9 milligrams, about 0.001 and about 49.9 milligrams, about 0.001 and about 19.9 milligrams, or about 0.001 and about 9.9 milligrams. Even more preferably, the dosage of MDL 100907 can be about 0.001 to about 0.5 mg.

APD125 (Arena Pharmaceuticals) can be used in any suitable dosage. For example, the dosage can be about 1 to about 160 milligrams, preferably about 5 to about 80 milligrams, or more preferably about 10 to about 40 milligrams. The dosage can between about 0.001 and about 159.9 milligrams, about 0.001 and about 79.9 milligrams, about 0.001 and about 39.9 milligrams, or about 0.001 and about 9.9 milligrams. Even more preferably, the dosage of ADP125 can be about 0.001 to about 5 mg.

AVE 8488 (Sanofi-Aventis) can be used in any suitable dosage. For example, the dosage can be about 0.5 to about 100 milligrams, preferably from about 1 to about 50 milligrams. The dosage can between about 0.001 and about 99.9 milligrams, about 0.001 and about 49.9 milligrams, about 0.001 and about 19.9 milligrams, or about 0.001 and about 9.9 milligrams. Even more preferably, the dosage of AVE 8488 can be about 0.001 to about 1 mg.

MN-305 (MediciNova) can be used in any suitable dosage. For example, the dosage can be about 0.1 to about 50 milligrams, preferably from about 0.5 to about 10 milligrams or 1-6 milligrams. The dosage can between about 0.001 and about 49.9 milligrams, about 0.001 and about 9.9 milligrams, about 0.001 and about 5.9 milligrams, about 0.001 and about 4.9, about 0.001 and about 3.9, about 0.001 and about 2.9 or about 0.001 and about 1.9 milligrams. For example, in some aspects the dosage of MN-305 can be about 1 mg, about 3 mg or about 6 mg. Even more preferably, the dosage of MN-305 can be about 0.001 to about 0.5 mg.

ORG 50081 (Organon; Akzo Novel) can be used in any suitable dosage. For example, the dosage can be about 0.5 to about 100 milligrams, preferably from about 1 to about 50 milligrams. The dosage can between about 0.001 and about 99.9 milligrams, about 0.001 and about 49.9 milligrams, about 0.001 and about 19.9 milligrams, or about 0.001 and about 9.9 milligrams. Even more preferably, the dosage of ORG 50081 can be about 0.001 to about 1 mg.

ACT-078573 (Actelion) can be used in any suitable dosage. For example, the dosage can be about 0.5 to about 100 milligrams, preferably from about 1 to about 50 milligrams. The dosage can between about 0.001 and about 99.9 milligrams, about 0.001 and about 49.9 milligrams, about 0.001 and about 19.9 milligrams, or about 0.001 and about 9.9 milligrams. Even more preferably, the dosage of ACT-078573 can be about 0.001 to about 1 mg.

Baclofen ((−)baclofen (β-(4-chloro-phenyl)-γ-aminobutyric acid) can be used in any suitable dosage. For example, the dosage can be about 1 mg to about 100 mg, preferably from, about 5 to about 40 mg. The dosage can between about 0.001 and about 99.9 milligrams, about 0.001 and about 39.9 milligrams, about 0.001 and about 19.9 milligrams, or about 0.001 and about 9.9 milligrams. Even more preferably, the dosage of baclofen can be about 0.001 to about 1 mg.

Eplivanserin can be used in any suitable dosage. For example, the dosage can be about 0.1 mg to about 20 mg. The dosage can between about 0.001 and about 19.9 milligrams, about 0.001 and about 9.9 milligrams, or about 0.001 and about 4.9 milligrams. Even more preferably the dosage can be about 0.001 mg to about 5 mg.

Pruvanserin (Eli Lilly) can be used in any suitable dosage. For example, the dosage can be about 0.1 mg to about 50 mg. The dosage can between about 0.001 and about 49.9 milligrams, about 0.001 and about 19.9 milligrams, or about 0.001 and about 9.9 milligrams. Even more preferably the dosage can be about 0.001 mg to about 10 mg.

ACT-078573 (Actelion; GlaxoSmithKline) can be used in any suitable dosage. For example, the dosage can be about 100 mg to about 1200 mg. The dosage can between about 0.001 and about 1199.9 milligrams, about 0.001 and about 999.9 milligrams, about 0.001 and about 499.9 milligrams, or about 0.001 and about 9.9 milligrams. Even more preferably the dosage can be about 0.001 mg to about 100 mg.

EVT 201 (Evotec) can be used in any suitable dosage. For example, the dosage can be about 0.01 mg to about 30 mg. The dosage can between about 0.001 and about 99.9 milligrams, about 0.001 and about 49.9 milligrams, about 0.001 and about 19.9 milligrams, or about 0.001 and about 9.9 milligrams. Even more preferably the dosage can be about 0.001 mg to about 1 mg.

Volinanserin (Sanofi-Aventis) can be used in any suitable dosage. For example, the dosage can be about 0.01 mg to about 20 mg. The dosage can between about 0.001 and about 19.9 milligrams, about 0.001 and about 9.9 milligrams, or about 0.001 and about 4.9 milligrams, or about 0.001 and about 1.9 milligrams. Even more preferably the dosage can be about 0.001 mg to about 2 mg.

HY10275 (Eli Lilly) can be used in any suitable dosage. For example, the dosage can be about 0.1 to about 50 milligrams, preferably from about 0.5 to about 10 milligrams or 1-6 milligrams. For example, in some aspects the dosage of HY10275 can be about 1 mg, about 3 mg or about 6 mg. The dosage can between about 0.001 and about 49.9 milligrams, about 0.001 and about 19.9 milligrams, about 0.001 and about 9.9 milligrams, about 0.001 and about 4.9 milligrams, about 0.001 and about 3.9 milligrams, about 0.001 and about 2.9 milligrams, about 0.001 and about 1.9 milligrams, or about 0.001 and about 0.9 milligrams. Even more preferably, the dosage of HY10275 can be about 0.001 to about 1 mg.

PD-6735 (6-chloro-(beta)-methyl melatonin; Phase II Discovery) can be used in any suitable dosage. For example, the dosage can be about 0.01 mg to about 150 mg. The dosage can between about 0.001 and about 149.9 milligrams, about 0.001 and about 99.9 milligrams, about 0.001 and about 49.9 milligrams, or about 0.001 and about 19.9 milligrams. Even more preferably the dosage can be about 0.001 mg to about 20 mg.

ITI-722 (Intracellular Therapies) can be used in any suitable dosage. For example, the dosage can be about 0.01 mg to about 500 mg. The dosage can between about 0.001 and about 499.9 milligrams, about 0.001 and about 99.9 milligrams, about 0.001 and about 49.9 milligrams, or about 0.001 and about 9.9 milligrams. Even more preferably the dosage can be about 0.001 mg to about 100 mg.

GW649868 (GlaxoSmithKline) can be used in any suitable dosage. Preferably, as an example, the dosage can be about 6.25-milligrams, 12.5 milligrams or a dosage that is a factor thereof, for example. The dosage can between about 0.001 and about 19.9 milligrams, about 0.001 and about 6.24 milligrams, about 0.001 and about 12.4 milligrams, or about 0.001 and about 4.9 milligrams. Even more preferably, the dosage of GW649868 can be less than 6.25 mg or 12.5 mg, for example between about 0.001 and 5 mg.

Casopitant (GlaxoSmithKline) can be used in any suitable dosage. For example, the dosage can be about 0.01 mg to about 500 mg. The dosage can between about 0.001 and about 499.9 milligrams, about 0.001 and about 99.9 milligrams, about 0.001 and about 49.9 milligrams, or about 0.001 and about 9.9 milligrams. Even more preferably the dosage can be about 0.001 mg to about 100 mg.

Circadin® (H. Lundbeck A/S) can be used in any suitable dosage. For example, the dosage can be about 0.01 mg to about 30 mg. The dosage can between about 0.001 and about 29.9 milligrams, about 0.001 and about 9.9 milligrams, about 0.001 and about 4.9 milligrams, or about 0.001 and about 1.9 milligrams. Even more preferably the dosage can be about 0.001 mg to about 2 mg.

Preparation and Administration of Drug Compositions

In performing the methods, a doxepin-related (doxepin, a pharmaceutically acceptable salt of doxepin or a doxepin prodrug) compound can be administered using any suitable route or method of delivery. Also, a doxepin-related compound can be administered alone or in combination with other substances, such as for example, other insomnia or sleep medications, or with other medications that treat a primary illness. For example, a doxepin-related compound can be administered with one or more of a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like. A doxepin-related compound alone or in combination can be included and administered as a composition.

In some embodiments, the drugs of the combination can be physically combined or mixed, together with suitable excipients. In others, they are separately contained in the same unit dosage form, but are physically separated. This includes unit dosage forms in which a single capsule, lozenge or tablet (such as a multilayer tablet or lozenge) contains two or more physically-separated drugs, which can be (for example) two layers or halves of a single tablet; a two-part capsule; or a capsule containing distinct particulate or bead forms of the individual drugs. Alternatively, the drugs of the combination can be physically separated in separate dosage forms, but packaged together; for example, in the same blister pack, or in the same primary or secondary container.

Suitable routes of administration include oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

For oral administration, the compounds can be formulated as pills, tablets, lozenges, powders, granules, dragees, capsules, liquids, sprays, gels, syrups, slurries, suspensions and the like, in bulk or unit dosage forms, for oral ingestion by a patient to be treated. The compounds can be formulated readily, for example, by combining the active compound with any suitable pharmaceutically acceptable carrier or excipient.

Pharmaceutical preparations for oral use can be obtained by mixing one or more solid excipients with a pharmaceutical composition as described herein, optionally grinding the resulting mixture, and processing the mixture of granules, after adding suitable auxiliaries, if desired, to obtain tablets or dragee cores. Suitable excipients are listed below. Some examples include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The formulation can be in form suitable for bolus administration, for example. Oral administration can be accomplished using fast-melt formulations, for example. As a further example, the formulations can be included in pre-measured ampules or syringes, push-fit capsules made of gelatin, as well as soft, sealed capsules made of gelatin and a plasticizer, such as glycerol or sorbitol. The push-fit capsules can contain a pharmaceutical composition as described herein in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, a pharmaceutical composition as described herein may take any suitable form, for example, tablets or lozenges.

For topical administration, a pharmaceutical composition as described herein may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

For injection, a pharmaceutical composition as described herein may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For administration by inhalation, a pharmaceutical composition as described herein for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

A pharmaceutical composition as described herein may be formulated for parenteral administration by injection, e.g., by bolus injection or continuous infusion. Formulations for injection may be presented in unit dosage form, e.g., in ampoules or in multi-dose containers, with an added preservative. The composition may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of a pharmaceutical composition as described herein may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition, any of the compounds and compositions described herein can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Furthermore, any of the compounds and compositions described herein also can be formulated as a fast-melt preparation. The compounds and compositions can also be formulated and administered as a drip, a suppository, a salve, an ointment, an absorbable material such a transdermal patch, or the like.

One can also administer a pharmaceutical composition as described herein in sustained release forms or from sustained release drug delivery systems. A description of representative sustained release materials can be found in the incorporated materials in *Remington: The Science and Practice of Pharmacy* (20$^{th}$ ed, Lippincott Williams & Wilkens Publishers (2003)), which is incorporated herein by reference in its entirety.

A variety of techniques for formulation and administration can be found in *Remington: The Science and Practice of Pharmacy* (20$^{th}$ ed, Lippincott Williams & Wilkens Publishers (2003)), which is incorporated herein by reference in its entirety.

As mentioned above, the compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* (2003). The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in *Remington: The Science and Practice of Pharmacy* (2003). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The compositions and formulations can include any other agents that provide improved transfer, delivery, tolerance, and the like. These compositions and formulations can include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Dosage

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved with an acceptable safety profile. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

As mentioned above, in some embodiments the dosage of the doxepin compound can be about 0.001 to about 0.49 milligrams, about 0.05 to about 24 milligrams, preferably about 0.5 to about 20 milligrams, and more preferably about 1 to about 10 milligrams. In some embodiments the preferable dosage of doxepin can be between about 1 milligram and 6 milligrams. Preferably, the dosage can be about 1 milligram, about 2 milligrams, about 3 milligrams, about 4 milligrams, about 5 milligrams, about 6 milligrams, about 7 milligrams, about 8 milligrams or about 9 milligrams.

Other sleep-promoting drugs in the combination are used in their art-recognized sleep-promoting dosages, in their approved dosages, their dosages used in clinical testing, laboratory testing, or in dosages reported in the scientific literature, or in higher doses or in smaller dosages than any of the aforementioned. In some aspects, the combinations can provide at the least equivalent sleep therapy benefit even when the amount of the sleep-promoting drug is less than the higher amount of that same drug that is needed to have the equivalent or lesser therapeutic benefit. Due to the co-action of the two drugs of the combination, a synergistic or complimentary activity results, so that the conventional monotherapy dosages of the drugs can be reduced by about any where from 5%, 10%, 20%, 30%, 40%, 50%, or more, for example.

Many modifications and variations of the embodiments described herein may be made without departing from the scope, as is apparent to those skilled in the art. The specific embodiments described herein are offered by way of example only.

EXAMPLES

Example 1

Doxepin is prepared by the following method.

(a) A Grignard compound is prepared in the conventional manner from 4.8 g (0.2 gram-atom) magnesium in 100 ml ether and 30 g (34 ml) (3-chloropropyl)-tertbutyl-ether and 16.40 grams (0.078 mol) 6,11-dihydrodibenzo-[b,e]-oxepine-11-one dissolved in 100 ml ether is added in dropwise fashion so that the contents of the flask boil lightly. The mixture is heated for 1 hour with agitation in a reflux condenser to complete the reaction and then it is decomposed with ammonium chloride solution. The product which is obtained by separating, drying and eliminating the solvent produced, when the ether residue (24.0 g) is extracted with ligroin, amounts to 20.3 g (80.0% of theory) of 11-(3-tertbutoxypropyl)-11-hydroxy-6,11-dihydrodibenzo-[b,e]-oxepine, having a melting point of 124-126° C. The (3-chloropropyl)-tertbutyl ether is thereafter obtained in the following manner: 19 g (0.2 mol) 1-chloropropanol-(3), 50 ml liquid isobutylene and 0.5 ml concentrated sulfuric acid are permitted to stand for 24 hours in an autoclave, then are poured into excess sodium bicarbonate solution and extracted with ether. The ether solution is dried with calcium chloride and distilled. 23.6 grams of (3-chloropropyl)-tert-butylether having a boiling point of 150-156° C. (78% of theory) are recovered.

(b) 30.8 grams of the 11-(3-tertbutoxypropyl)-11-hydroxy-6,11-dihydro dibenzo-[b,e]-oxepine obtained according to (a) above and 150 ml absolute alcoholic hydrochloric acid are heated for 1 hour at ebullition. After removing the solvent by evaporation, the residue is crystallized with ligroin, 21.0 grams (88.5% of theory) of 11-(3-hydroxypropylidene)-6,11-dihydrodibenzo-[b,e]-oxepine having a melting point of 108-111° C. were obtained. After recrystallization from acetic acid ester, the compound melts at 112-114° C.

(c) 5.0 ml thionyl chloride dissolved in 5 ml benzene is added dropwise at room temperature to 12.6 g (0.05 mol) of the 11-(3-hydroxypropylidene)-6,11-dihydrodibenzo-[b,e]-oxepine obtained in part (b) above. After 1 hour of standing, the contents of the flask are heated at ebullition for 2 hours. The volatile components are thereafter removed and the remainder distilled using high vacuum. The yield amounts to 10.6 g (78.5% of theory) of 11-(3-chloropropylidene)-6,11-dihydrodibenzo-[b,e]-oxepine having a B.P.0.1 169-172° C., a melting point of 106-111° C. After recrystallization from 20 ml of acetic acid ester, 9.1 g (67.5% of theory) of pure product having a melting point of 113-115° C. is obtained. The crude product can however be used quite easily for further processing.

(d) 5.4 g (0.02 mol) of the 11-(3-chloropropylidene)-6,11-dihydrodibenzo-[b,e]-oxepine, prepared according to (c) above, in 20 ml tetrahydrofuran and 5.5 g (0.12 mol) dimethylamine in 20 ml ethanol is heated together for 3 hours using a glass autoclave and a temperature of 95-100° C. (boiling water bath). Water and 6 N hydrochloric acid are added to the contents of the autoclave and the mixture is extracted with ether. The separated, aqueous-acid components are then made alkaline with dilute caustic soda solution, and the oil thereby separated is taken up in ether. The ether residue, after distillation in a high vacuum, produces 4.1 g (73.5% of theory) of 11-(3-dimethylamino-propylidene)-6,11-dihydrodibenzo-[b,e]-oxepine, having a B.P.$_{0.1}$ 147-150° C. The melting point of the hydrochloride is 182-184° C. (recrystallized from isopropanol).

Example 2

The patient suffers from transient or short-term insomnia. At the time of consultation, he is otherwise healthy with normal affect with no depression, anxiety or substance overuse. He is prescribed a doxepin or a pharmaceutically acceptable salt or prodrug thereof and one or more of a compound that modulates gamma-aminobutyric acid (GABA) activity (e.g., enhances the activity), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, and the like, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 3

The patient suffers from chronic insomnia. At the time of consultation, he is otherwise healthy with normal affect with no depression, anxiety or substance overuse. He is prescribed a doxepin or a pharmaceutically acceptable salt or prodrug thereof and one or more of a compound that modulates gamma-aminobutyric acid (GABA) activity (e.g., enhances the activity), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, and the like, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 4

The patient suffers from maintenance (non-chronic) insomnia. At the time of consultation, he is otherwise healthy with normal affect with no depression, anxiety or substance overuse. He is prescribed a doxepin or a pharmaceutically acceptable salt or prodrug thereof and one or more of a compound that modulates gamma-aminobutyric acid (GABA) activity (e.g., enhances the activity), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, and the like, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 5

The patient suffers from onset (non-chronic) insomnia. At the time of consultation, he is otherwise healthy with normal affect with no depression, anxiety or substance overuse. He is prescribed a doxepin or a pharmaceutically acceptable salt or prodrug thereof and one or more of a compound that modulates gamma-aminobutyric acid (GABA) activity (e.g., enhances the activity), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, and the like, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 6

The patient suffers from a sleep disorder. At the time of consultation, he also suffers from depression. He is prescribed a doxepin or a pharmaceutically acceptable salt or prodrug thereof and one or more of a compound that modulates gamma-aminobutyric acid (GABA) activity (e.g., enhances the activity), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker) a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, and the like, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the sleep disorder and has him sleeping well.

Example 7

The patient suffers from a sleep disorder. At the time of consultation, he is otherwise healthy with normal affect with no depression, anxiety or substance overuse. He is prescribed a doxepin or a pharmaceutically acceptable salt or prodrug thereof and one or more of a compound that modulates gamma-aminobutyric acid (GABA) activity or a GABA-B agonist. Follow up reveals that the administration of the combination doxepin or the pharmaceutically acceptable salt or prodrug thereof and the compound relieves the sleep disorder and has him sleeping well.

Example 8

The patient suffers from a sleep disorder. At the time of consultation, he is otherwise healthy with normal affect with no depression, anxiety or substance overuse. He is prescribed a doxepin or a pharmaceutically acceptable salt or prodrug thereof and a 5-HT modulator (e.g., a 5-HT1a agonist, a 5-HT2a antagonist, a 5-HT2a inverse agonist, etc.). Follow up reveals that the administration of the combination doxepin or the pharmaceutically acceptable salt or prodrug thereof and the 5-HT modulator relieves the sleep disorder and has him sleeping well.

Example 9

The patient suffers from a sleep disorder. At the time of consultation, he is otherwise healthy with normal affect with no depression, anxiety or substance overuse. He is prescribed a doxepin or a pharmaceutically acceptable salt or prodrug thereof and a melatonin agonist. Follow up reveals that the administration of the combination doxepin or the pharmaceutically acceptable salt or prodrug thereof and the melatonin agonist relieves the sleep disorder and has him sleeping well.

Example 10

The patient suffers from a sleep disorder. At the time of consultation, he is otherwise healthy with normal affect with no depression, anxiety or substance overuse. He is prescribed a doxepin or a pharmaceutically acceptable salt or prodrug thereof and an ion channel modulator. Follow up reveals that the administration of the combination doxepin or the pharmaceutically acceptable salt or prodrug thereof and the ion channel modulator relieves the sleep disorder and has him sleeping well.

Example 11

The patient suffers from a sleep disorder. At the time of consultation, he is otherwise healthy with normal affect with no depression, anxiety or substance overuse. He is prescribed a doxepin or a pharmaceutically acceptable salt or prodrug thereof and a serotonin-2 antagonist/reuptake inhibitor (SARIs). Follow up reveals that the administration of the combination doxepin or the pharmaceutically acceptable salt or prodrug thereof and the serotonin-2 antagonist/reuptake inhibitor (SARIS) relieves the sleep disorder and has him sleeping well.

Example 12

The patient suffers from a sleep disorder. At the time of consultation, he is otherwise healthy with normal affect with no depression, anxiety or substance overuse. He is prescribed a doxepin or a pharmaceutically acceptable salt or prodrug thereof and an orexin receptor antagonist. Follow up reveals that the administration of the combination doxepin or the pharmaceutically acceptable salt or prodrug thereof and the orexin receptor antagonist relieves the sleep disorder and has him sleeping well.

Example 13

The patient suffers from a sleep disorder. At the time of consultation, he is otherwise healthy with normal affect with no depression, anxiety or substance overuse. He is prescribed a doxepin or a pharmaceutically acceptable salt or prodrug thereof and an H3 agonist. Follow up reveals that the administration of the combination doxepin or the pharmaceutically acceptable salt or prodrug thereof and the H3 agonist relieves the sleep disorder and has him sleeping well.

Example 14

The patient suffers from a sleep disorder. At the time of consultation, he is otherwise healthy with normal affect with no depression, anxiety or substance overuse. He is prescribed a doxepin or a pharmaceutically acceptable salt or prodrug thereof and a noradrenergic antagonist. Follow up reveals that the administration of the combination doxepin or the pharmaceutically acceptable salt or prodrug thereof and the noradrenergic antagonist relieves the sleep disorder and has him sleeping well.

Example 15

The patient suffers from a sleep disorder. At the time of consultation, he is otherwise healthy with normal affect with no depression, anxiety or substance overuse. He is prescribed a doxepin or a pharmaceutically acceptable salt or prodrug thereof and a galanin agonist. Follow up reveals that the administration of the combination doxepin or the pharmaceutically acceptable salt or prodrug thereof and the galanin agonist relieves the sleep disorder and has him sleeping well.

Example 16

The patient suffers from transient or short-term insomnia. At the time of consultation, he also suffers from or is at risk of suffering from substance abuse. He is prescribed doxepin or a pharmaceutically acceptable salt or prodrug thereof and a melatonin agonist, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 17

The patient suffers from transient or short-term insomnia. At the time of consultation, he also suffers from or is at risk of suffering from alcoholism. He is prescribed doxepin or a pharmaceutically acceptable salt or prodrug thereof and a melatonin agonist, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 18

The patient suffers from transient or short-term insomnia. At the time of consultation, he is also being administered a narcotic medication. He is prescribed doxepin or a pharmaceutically acceptable salt or prodrug thereof and a melatonin agonist, wherein the doxepin or the pharmaceutically acceptable salt or prodrug thereof is in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the combination doxepin or the pharmaceutically acceptable salt or prodrug thereof and the compound relieves the insomnia and has him sleeping well.

Example 19

The patient suffers from a sleep disorder. At the time of consultation, the patient experiences or has experienced undesirable side effects associated with administration of one or more of a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like in a first dosage effective at treating the sleep disorder. He is prescribed doxepin or a pharmaceutically acceptable salt or prodrug thereof and one or more drugs selected from a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like, wherein the one or more of a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like, wherein the one or more drugs are present in a dosage less than the first dosage. Follow up reveals that the administration of the combination doxepin or the pharmaceutically acceptable salt or prodrug thereof and the drug is effective in treating the sleep disorder and reduces the experience of the undesirable side effect.

Example 20

The patient suffers from onset and maintenance insomnia. Doxepin is effective at treating the maintenance insomnia but is not effective or only partially effective at treating the onset insomnia. The patient is prescribed doxepin or a pharmaceutically acceptable salt or prodrug thereof and one or more drugs selected from a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like, wherein the one or more of a GABA-B agonist, a 5-HT modulator (e.g., a 5-HT1a agonist, a 5-HT2a antagonist, a 5-HT2a inverse agonist, etc.), an ion channel modulator (e.g., blocker) a serotonin-2 antagonist/reuptake inhibitor (SARIs), a noradrenergic antagonist, a CRH antagonist, human growth hormone, a growth hormone agonist, estrogen, an estrogen agonist, a neurokinin-1 drug, and the like, wherein the one or more drugs are present in a dosage less than the first dosage. Follow up reveals that the administration of the combination doxepin or the pharmaceutically acceptable salt or prodrug thereof and the drug is effective in treating both the onset insomnia and the maintenance insomnia.

We claim:

1. A method of treating insomnia in a human patient in need thereof, the method comprising:
   administering to the patient a composition consisting essentially of:
   about 0.5 mg to about 7 mg of doxepin hydrochloride;
   about 0.1 mg to about 4.5 mg of zolpidem tartrate; and
   one or more pharmaceutical excipients.

2. The method of claim 1, wherein the composition comprises between about 0.5 mg and about 6 mg of doxepin hydrochloride.

3. The method of claim 2, wherein the composition comprises between about 1 mg and about 6 mg of doxepin hydrochloride.

4. The method of claim 3, wherein the composition comprises about 1 mg of doxepin hydrochloride.

5. The method of claim 3, wherein the composition comprises about 3 mg of doxepin hydrochloride.

6. The method of claim 3, wherein the composition comprises about 6 mg of doxepin hydrochloride.

7. The method of claim 1, wherein the composition is administered by an oral, buccal, sublingual, transdermal, rectal, topical, transmucosal, intestinal or parenteral route of administration.

8. The method of claim 1, wherein the one or more excipient is selected from the group consisting of: diluents, disintegrants, binding agents, adhesives, wetting agents, polymers, lubricants, glidants, substances added to mask or counteract a disagreeable taste or odor, flavors, dyes, fragrances, and substances added to improve appearance of the composition.

9. The method of claim 1, wherein the one or more excipient is selected from the group consisting of: lactose, sucrose, mannitol, sorbitol, other sugars, starch powder, maize starch or derivatives thereof, wheat starch, rice starch, potato starch, gelatin, gum tragacanth, methyl cellulose, hydroxypropylmethyl cellulose, sodium carboxymethylcellulose, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, polyvinyl alcohol, saline, dextrose, lecithin, albumin, sodium glutamate, and cysteine hydrochloride.

* * * * *